(12) United States Patent
Humayun et al.

(10) Patent No.: US 10,117,774 B2
(45) Date of Patent: Nov. 6, 2018

(54) APPARATUS AND METHODS FOR DELIVERING THERAPEUTIC AGENTS

(71) Applicant: University of Southern California, Los Angeles, CA (US)

(72) Inventors: Mark S. Humayun, Glendale, CA (US); Sean Caffey, Pasadena, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 1052 days.

(21) Appl. No.: 13/931,007

(22) Filed: Jun. 28, 2013

(65) Prior Publication Data

US 2013/0296810 A1 Nov. 7, 2013

Related U.S. Application Data

(62) Division of application No. 12/340,095, filed on Dec. 19, 2008, now Pat. No. 9,308,124.

(60) Provisional application No. 61/015,509, filed on Dec. 20, 2007, provisional application No. 61/197,750, filed on Oct. 30, 2008.

(51) Int. Cl.
  *A61F 9/00* (2006.01)
  *A61M 31/00* (2006.01)

(52) U.S. Cl.
  CPC .......... *A61F 9/0017* (2013.01); *A61F 9/0026* (2013.01); *A61M 31/002* (2013.01); *A61F 2250/0068* (2013.01)

(58) Field of Classification Search
  None
  See application file for complete search history.

(56) References Cited

U.S. PATENT DOCUMENTS

| | | | |
|---|---|---|---|
| 2,445,477 A | | 7/1948 | Folkman |
| 3,043,303 A | * | 7/1962 | Still .................... A61B 5/0002 |
| | | | 600/578 |
| 3,175,558 A | | 3/1965 | Caillonette et al. |
| 3,731,681 A | | 5/1973 | Varco et al. |
| 3,760,805 A | | 9/1973 | Higuchi |
| 3,894,538 A | | 7/1975 | Richter |
| 3,916,899 A | | 11/1975 | Theeuwes et al. |
| 3,977,404 A | | 8/1976 | Theeuwes |
| 4,102,492 A | * | 7/1978 | Gold .................... G05B 19/124 |
| | | | 200/46 |
| 4,140,121 A | | 2/1979 | Kuhl et al. |
| 4,140,122 A | | 2/1979 | Kuhl et al. |
| 4,150,673 A | | 4/1979 | Watt |

(Continued)

FOREIGN PATENT DOCUMENTS

CN 103108665 A 5/2013
CN 102202708 B 1/2015

(Continued)

OTHER PUBLICATIONS

"FDA Approves and Industry First!—The MED-EL Cochlear Implant System in FDA Approved for Use With Magnetic Resonance Imaging (MRI)," PR Newswire, Durham, N.C., Jun. 18, 2003, 3 pages.

(Continued)

*Primary Examiner* — Paula L Craig
(74) *Attorney, Agent, or Firm* — Morgan, Lewis & Bockius LLP

(57) ABSTRACT

In various embodiments, a drug-delivery device includes one or more reservoirs that may each contain a therapeutic agent for delivery to a patient.

20 Claims, 18 Drawing Sheets

(56) References Cited

U.S. PATENT DOCUMENTS

| | | | |
|---|---|---|---|
| 4,164,560 A | 8/1979 | Folkman et al. | |
| 4,180,375 A | 12/1979 | Magnussen, Jr. | |
| 4,203,441 A | 5/1980 | Theeuwes | |
| 4,237,881 A | 12/1980 | Beigler et al. | |
| 4,300,554 A | 11/1981 | Hessberg et al. | |
| 4,305,399 A * | 12/1981 | Beale | A61B 3/16 336/115 |
| 4,373,527 A | 2/1983 | Fischell | |
| 4,375,228 A | 3/1983 | Widdowson | |
| 4,543,088 A | 9/1985 | Bootman et al. | |
| 4,553,973 A | 11/1985 | Edgren | |
| 4,559,036 A * | 12/1985 | Wunsch | A61M 5/16827 604/247 |
| 4,576,592 A * | 3/1986 | Danby | A61M 5/16827 604/253 |
| 4,604,093 A * | 8/1986 | Brown | A61M 5/16827 137/625.11 |
| 4,692,145 A | 9/1987 | Weyant | |
| 4,738,657 A | 4/1988 | Hancock et al. | |
| 4,751,926 A | 6/1988 | Sasaki | |
| 4,760,837 A | 8/1988 | Petit | |
| 4,781,675 A | 11/1988 | White | |
| 4,781,695 A | 11/1988 | Dalton | |
| 4,804,054 A | 2/1989 | Howson et al. | |
| 4,838,887 A | 6/1989 | Idriss | |
| 4,853,224 A | 8/1989 | Wong | |
| 4,886,499 A | 12/1989 | Cirelli et al. | |
| 4,888,176 A | 12/1989 | Langer et al. | |
| 4,902,278 A | 2/1990 | Maget et al. | |
| 4,922,913 A * | 5/1990 | Waters, Jr. | A61B 3/16 600/398 |
| 4,923,457 A | 5/1990 | Ellingsen | |
| 4,935,009 A * | 6/1990 | Caldwell | A61M 5/1424 604/218 |
| 4,944,659 A | 7/1990 | Labbe et al. | |
| 4,959,217 A | 9/1990 | Sanders et al. | |
| 4,969,874 A | 11/1990 | Michel et al. | |
| 5,005,577 A * | 4/1991 | Frenkel | A61B 3/16 600/398 |
| 5,045,064 A | 9/1991 | Idriss | |
| 5,062,834 A | 11/1991 | Gross et al. | |
| 5,066,276 A | 11/1991 | Wang | |
| 5,067,491 A | 11/1991 | Taylor, II et al. | |
| 5,090,963 A | 2/1992 | Gross et al. | |
| 5,108,372 A | 4/1992 | Swenson | |
| 5,135,498 A | 8/1992 | Kam et al. | |
| 5,135,499 A | 8/1992 | Tafani et al. | |
| 5,147,647 A | 9/1992 | Darougar | |
| 5,163,909 A | 11/1992 | Stewart | |
| 5,164,188 A | 11/1992 | Wong | |
| 5,171,213 A | 12/1992 | Price, Jr. | |
| 5,178,604 A | 1/1993 | Baerveldt et al. | |
| 5,207,227 A | 5/1993 | Powers | |
| 5,207,642 A * | 5/1993 | Orkin | A61M 5/16827 128/DIG. 13 |
| 5,213,568 A | 5/1993 | Lattin et al. | |
| 5,242,406 A | 9/1993 | Gross et al. | |
| 5,242,408 A | 9/1993 | Jhuboo et al. | |
| 5,252,192 A | 10/1993 | Ludwig | |
| 5,279,607 A | 1/1994 | Schentag et al. | |
| 5,318,540 A | 6/1994 | Athayde et al. | |
| 5,318,557 A | 6/1994 | Gross | |
| 5,354,264 A | 10/1994 | Bae et al. | |
| 5,368,571 A | 11/1994 | Horres, Jr. | |
| 5,399,166 A | 3/1995 | Laing | |
| 5,407,441 A | 4/1995 | Greenbaum | |
| 5,425,716 A | 6/1995 | Kawasaki et al. | |
| 5,443,505 A | 8/1995 | Wong et al. | |
| 5,458,095 A | 10/1995 | Post et al. | |
| 5,462,739 A | 10/1995 | Dan et al. | |
| 5,472,436 A | 12/1995 | Fremstad | |
| 5,474,527 A | 12/1995 | Bettinger | |
| 5,476,445 A | 12/1995 | Baerveldt et al. | |
| 5,505,697 A | 4/1996 | McKinnon et al. | |
| 5,527,288 A | 6/1996 | Gross et al. | |
| 5,553,741 A | 9/1996 | Sancoff et al. | |
| 5,616,219 A | 4/1997 | Patterson | |
| 5,629,008 A | 5/1997 | Lee | |
| 5,676,651 A | 10/1997 | Larson, Jr. et al. | |
| 5,704,520 A | 1/1998 | Gross | |
| 5,707,499 A | 1/1998 | Joshi et al. | |
| 5,713,857 A | 2/1998 | Grimard et al. | |
| 5,725,017 A | 3/1998 | Elsberry et al. | |
| 5,725,493 A | 3/1998 | Avery et al. | |
| 5,741,275 A | 4/1998 | Wyssmann | |
| 5,782,799 A | 7/1998 | Jacobsen et al. | |
| 5,785,681 A | 7/1998 | Indravudh | |
| 5,785,688 A | 7/1998 | Joshi et al. | |
| 5,788,682 A | 8/1998 | Maget | |
| 5,798,114 A | 8/1998 | Elsberry et al. | |
| 5,798,115 A | 8/1998 | Santerre et al. | |
| 5,800,420 A | 9/1998 | Gross et al. | |
| 5,824,072 A | 10/1998 | Wong | |
| 5,830,173 A | 11/1998 | Avery et al. | |
| 5,836,935 A | 11/1998 | Ashton et al. | |
| 5,855,761 A * | 1/1999 | Joshi | A61M 5/14526 205/615 |
| 5,868,697 A | 2/1999 | Richter et al. | |
| 5,891,097 A | 4/1999 | Saito et al. | |
| 5,904,144 A | 5/1999 | Hammang et al. | |
| 5,951,538 A | 9/1999 | Joshi et al. | |
| 5,989,579 A | 11/1999 | Darougar et al. | |
| 5,993,374 A | 11/1999 | Kick | |
| 6,048,328 A | 4/2000 | Haller et al. | |
| 6,129,696 A | 10/2000 | Sibalis | |
| 6,139,520 A * | 10/2000 | McCrory | A61B 17/12022 128/898 |
| 6,144,106 A | 11/2000 | Bearinger et al. | |
| 6,203,523 B1 | 3/2001 | Haller et al. | |
| 6,240,962 B1 | 6/2001 | Tai et al. | |
| 6,251,090 B1 | 6/2001 | Avery et al. | |
| 6,254,586 B1 | 7/2001 | Mann et al. | |
| 6,264,971 B1 | 7/2001 | Darougar et al. | |
| 6,281,192 B1 | 8/2001 | Leahy et al. | |
| 6,287,295 B1 | 9/2001 | Chen et al. | |
| 6,364,865 B1 * | 4/2002 | Lavi | A61J 1/2089 604/411 |
| 6,370,970 B1 | 4/2002 | Hosokawa et al. | |
| 6,375,972 B1 | 4/2002 | Guo et al. | |
| 6,390,791 B1 | 5/2002 | Maillefer et al. | |
| 6,408,878 B2 | 6/2002 | Unger et al. | |
| 6,413,238 B1 * | 7/2002 | Maget | A61M 5/14526 604/132 |
| 6,416,777 B1 | 7/2002 | Yaacobi | |
| 6,450,991 B1 * | 9/2002 | Bunt | A61D 7/00 604/141 |
| 6,458,102 B1 | 10/2002 | Mann et al. | |
| 6,491,684 B1 | 12/2002 | Joshi et al. | |
| 6,520,936 B1 | 2/2003 | Mann | |
| 6,527,744 B1 | 3/2003 | Kriesel et al. | |
| 6,537,268 B1 | 3/2003 | Gibson et al. | |
| 6,544,193 B2 * | 4/2003 | Abreu | A61B 3/1241 600/558 |
| 6,558,361 B1 | 5/2003 | Yeshurun | |
| 6,575,961 B2 | 6/2003 | Joshi | |
| 6,577,899 B2 * | 6/2003 | Lebel | A61N 1/37211 128/903 |
| 6,589,205 B1 | 7/2003 | Meadows | |
| 6,669,950 B2 | 12/2003 | Yaacobi | |
| 6,697,694 B2 | 2/2004 | Mogensen | |
| 6,699,394 B2 | 3/2004 | Tai et al. | |
| 6,713,081 B2 | 3/2004 | Robinson et al. | |
| 6,719,750 B2 | 4/2004 | Varner et al. | |
| 6,817,252 B2 | 11/2004 | Wiklund et al. | |
| 6,852,097 B1 | 2/2005 | Fulton, III | |
| 6,852,106 B2 | 2/2005 | Watson et al. | |
| 6,899,137 B2 | 5/2005 | Unger et al. | |
| 6,948,918 B2 | 9/2005 | Hansen | |
| 6,955,670 B2 | 10/2005 | Martin et al. | |
| 6,973,718 B2 | 12/2005 | Sheppard, Jr. et al. | |
| 7,070,577 B1 | 7/2006 | Haller et al. | |
| 7,090,471 B2 | 8/2006 | Xie et al. | |
| 7,225,683 B2 | 6/2007 | Harnett et al. | |

(56) References Cited

U.S. PATENT DOCUMENTS

| | | |
|---|---|---|
| 7,276,050 B2 | 10/2007 | Franklin |
| 7,351,303 B2 | 4/2008 | Liu et al. |
| 7,429,258 B2 | 9/2008 | Angel et al. |
| 7,470,267 B2 | 12/2008 | Joshi et al. |
| 7,517,440 B2 | 4/2009 | Anex et al. |
| 7,524,304 B2 | 4/2009 | Genosar |
| 7,537,590 B2 | 5/2009 | Santini, Jr. et al. |
| 7,544,190 B2 | 6/2009 | Pickup et al. |
| 7,600,533 B2 * | 10/2009 | Tai ............... F16K 99/0005 137/516.25 |
| 7,606,615 B2 | 10/2009 | Makower et al. |
| 7,766,873 B2 | 8/2010 | Moberg et al. |
| 7,828,771 B2 | 11/2010 | Chiang et al. |
| 7,867,203 B2 | 1/2011 | Rosenberg et al. |
| 7,887,508 B2 | 2/2011 | Meng et al. |
| 7,931,643 B2 | 4/2011 | Olsen et al. |
| 8,083,710 B2 * | 12/2011 | Hood ............... A61M 37/0092 604/65 |
| 8,147,447 B2 | 4/2012 | Sundar et al. |
| 8,231,608 B2 | 7/2012 | Pang et al. |
| 8,231,609 B2 | 7/2012 | Pang et al. |
| 8,246,569 B1 | 8/2012 | Meng et al. |
| 8,285,328 B2 | 10/2012 | Caffey et al. |
| 8,308,686 B2 | 11/2012 | Meng et al. |
| 8,486,278 B2 | 7/2013 | Pang et al. |
| 8,529,538 B2 | 9/2013 | Pang et al. |
| 8,585,648 B2 | 11/2013 | Caffey |
| 8,684,997 B2 | 4/2014 | Pang et al. |
| 8,764,708 B2 | 7/2014 | Tai et al. |
| 8,920,376 B2 | 12/2014 | Caffey et al. |
| 9,271,866 B2 * | 3/2016 | Humayun ............ A61F 9/0017 |
| 9,308,124 B2 * | 4/2016 | Humayun ............ A61F 9/0017 |
| 2001/0053891 A1 * | 12/2001 | Ackley ............ A61M 37/0015 604/191 |
| 2002/0016569 A1 | 2/2002 | Critchlow et al. |
| 2002/0026176 A1 | 2/2002 | Varner et al. |
| 2002/0040208 A1 | 4/2002 | Flaherty et al. |
| 2002/0049389 A1 * | 4/2002 | Abreu ............... A61B 3/1241 600/558 |
| 2002/0103412 A1 | 8/2002 | Trimmer |
| 2002/0156462 A1 | 10/2002 | Stultz |
| 2002/0188282 A1 | 12/2002 | Greenberg |
| 2003/0014014 A1 | 1/2003 | Nitzan |
| 2003/0014036 A1 | 1/2003 | Varner et al. |
| 2003/0064088 A1 | 4/2003 | Carvalho et al. |
| 2003/0069560 A1 | 4/2003 | Adamis et al. |
| 2003/0141618 A1 | 7/2003 | Braithwaite et al. |
| 2003/0171710 A1 * | 9/2003 | Bassuk ............... A61M 31/002 604/67 |
| 2003/0208167 A1 * | 11/2003 | Prausnitz ............ A61B 5/1411 604/272 |
| 2004/0028655 A1 | 2/2004 | Nelson et al. |
| 2004/0096410 A1 | 5/2004 | Maley et al. |
| 2004/0100528 A1 | 5/2004 | Howkins et al. |
| 2004/0106914 A1 | 6/2004 | Coppeta et al. |
| 2004/0116794 A1 * | 6/2004 | Fink ............... A61B 3/16 600/398 |
| 2004/0116905 A1 | 6/2004 | Pedersen et al. |
| 2004/0126253 A1 | 7/2004 | Gray et al. |
| 2004/0143221 A1 | 7/2004 | Shadduck |
| 2004/0175410 A1 | 9/2004 | Ashton et al. |
| 2004/0188648 A1 | 9/2004 | Xie et al. |
| 2004/0199130 A1 | 10/2004 | Chornenky et al. |
| 2004/0208910 A1 | 10/2004 | Ashton et al. |
| 2004/0228734 A1 | 11/2004 | Jeon et al. |
| 2004/0243101 A1 * | 12/2004 | Gillis ............... A61M 25/0043 604/523 |
| 2005/0010175 A1 | 1/2005 | Beedon et al. |
| 2005/0054988 A1 | 3/2005 | Rosenberg et al. |
| 2005/0065500 A1 | 3/2005 | Couvillon et al. |
| 2005/0076242 A1 | 4/2005 | Breuer |
| 2005/0096707 A1 | 5/2005 | Hill et al. |
| 2005/0106225 A1 | 5/2005 | Massengale et al. |
| 2005/0175708 A1 | 8/2005 | Carrasquillo et al. |
| 2005/0187515 A1 | 8/2005 | Varrichio et al. |
| 2005/0208103 A1 | 9/2005 | Adamis et al. |
| 2005/0209562 A1 | 9/2005 | Kim |
| 2005/0214129 A1 | 9/2005 | Greene et al. |
| 2005/0277912 A1 * | 12/2005 | John ............... A61M 25/0026 604/890.1 |
| 2006/0012280 A1 | 1/2006 | Kang et al. |
| 2006/0014793 A1 | 1/2006 | Nakamura et al. |
| 2006/0047538 A1 | 3/2006 | Condurso et al. |
| 2006/0052666 A1 | 3/2006 | Kumar et al. |
| 2006/0052768 A1 | 3/2006 | Joshi et al. |
| 2006/0069382 A1 | 3/2006 | Pedersen |
| 2006/0075016 A1 | 4/2006 | Kanayama et al. |
| 2006/0089619 A1 | 4/2006 | Ginggen |
| 2006/0116641 A1 | 6/2006 | Gordon et al. |
| 2006/0167435 A1 | 7/2006 | Adamis et al. |
| 2006/0178655 A1 | 8/2006 | Santini et al. |
| 2006/0178665 A1 | 8/2006 | Sloan et al. |
| 2006/0178709 A1 * | 8/2006 | Foster ............... A61M 5/14276 607/45 |
| 2006/0200097 A1 | 9/2006 | Humayun et al. |
| 2006/0224100 A1 | 10/2006 | Gertner |
| 2006/0235428 A1 | 10/2006 | Silvestrini |
| 2006/0258994 A1 | 11/2006 | Avery |
| 2006/0259015 A1 | 11/2006 | Steinbach |
| 2006/0271020 A1 | 11/2006 | Huang et al. |
| 2007/0021735 A1 | 1/2007 | Bhavaraju et al. |
| 2007/0060870 A1 | 3/2007 | Tolle et al. |
| 2007/0066939 A1 | 3/2007 | Krulevitch et al. |
| 2007/0073267 A1 * | 3/2007 | Muller ............... A61M 5/1408 604/506 |
| 2007/0084765 A1 | 4/2007 | Tse |
| 2007/0093752 A1 | 4/2007 | Zhao et al. |
| 2007/0106199 A1 | 5/2007 | Krivoy et al. |
| 2007/0106218 A1 | 5/2007 | Yodfat et al. |
| 2007/0106557 A1 | 5/2007 | Varghese |
| 2007/0112328 A1 | 5/2007 | Steinbach et al. |
| 2007/0118066 A1 | 5/2007 | Pinchuk et al. |
| 2007/0135765 A1 * | 6/2007 | Miller ............... A61M 5/16827 604/131 |
| 2007/0173900 A1 | 7/2007 | Siegel et al. |
| 2007/0191770 A1 | 8/2007 | Moberg et al. |
| 2007/0228071 A1 | 10/2007 | Kamen et al. |
| 2007/0250045 A1 * | 10/2007 | Trieu ............... A61B 17/58 604/890.1 |
| 2007/0255233 A1 | 11/2007 | Haase |
| 2007/0255235 A1 | 11/2007 | Olsen et al. |
| 2007/0255250 A1 | 11/2007 | Moberg et al. |
| 2007/0255261 A1 | 11/2007 | Haase |
| 2007/0269487 A1 | 11/2007 | de Juan et al. |
| 2007/0270760 A1 * | 11/2007 | Dacquay ............ A61F 9/0017 604/208 |
| 2007/0275384 A1 | 11/2007 | Leppert et al. |
| 2008/0015494 A1 | 1/2008 | Santini et al. |
| 2008/0022789 A1 | 1/2008 | Okuno et al. |
| 2008/0033255 A1 | 2/2008 | Essenpreis et al. |
| 2008/0035875 A1 * | 2/2008 | Tai ............... F16K 99/0005 251/318 |
| 2008/0039768 A1 | 2/2008 | Francis |
| 2008/0039792 A1 * | 2/2008 | Meng ............... A61K 9/0024 604/114 |
| 2008/0097412 A1 | 4/2008 | Shuros et al. |
| 2008/0102119 A1 | 5/2008 | Grovender et al. |
| 2008/0119707 A1 | 5/2008 | Stafford |
| 2008/0170936 A1 | 7/2008 | Den Toonder et al. |
| 2008/0181930 A1 | 7/2008 | Rodstrom et al. |
| 2008/0194053 A1 | 8/2008 | Huang |
| 2008/0210306 A1 | 9/2008 | Xie et al. |
| 2008/0234637 A1 | 9/2008 | McConnell et al. |
| 2008/0243071 A1 | 10/2008 | Quijano et al. |
| 2008/0257410 A1 | 10/2008 | Walborn |
| 2008/0269664 A1 | 10/2008 | Trovato et al. |
| 2008/0275384 A1 | 11/2008 | Mastrototaro |
| 2008/0312584 A1 | 12/2008 | Montgomery et al. |
| 2009/0028824 A1 | 1/2009 | Chiang et al. |
| 2009/0041624 A1 | 2/2009 | Hochmuth et al. |
| 2009/0112188 A1 | 4/2009 | Santini, Jr. et al. |
| 2009/0163860 A1 | 6/2009 | Patrick et al. |

(56) References Cited

U.S. PATENT DOCUMENTS

| | | | |
|---|---|---|---|
| 2009/0188576 A1 | 7/2009 | Kang et al. |
| 2009/0192493 A1 | 7/2009 | Meng et al. |
| 2009/0205399 A1 | 8/2009 | Sun et al. |
| 2009/0227855 A1 | 9/2009 | Hill et al. |
| 2009/0234366 A1 | 9/2009 | Tsai et al. |
| 2009/0234594 A1 | 9/2009 | Carlisle et al. |
| 2009/0240215 A1 | 9/2009 | Humayun et al. |
| 2009/0240232 A1* | 9/2009 | Gonnelli ........... A61M 5/14526 604/506 |
| 2009/0259176 A1 | 10/2009 | Yairi |
| 2009/0281528 A1 | 11/2009 | Grovender et al. |
| 2009/0306585 A1 | 12/2009 | Pang et al. |
| 2009/0306594 A1 | 12/2009 | Pang et al. |
| 2009/0306595 A1 | 12/2009 | Shih et al. |
| 2009/0306633 A1 | 12/2009 | Trovato et al. |
| 2009/0308752 A1 | 12/2009 | Evans et al. |
| 2009/0311133 A1 | 12/2009 | Pang et al. |
| 2009/0312742 A1 | 12/2009 | Pang et al. |
| 2010/0004639 A1 | 1/2010 | Pang et al. |
| 2010/0030550 A1 | 2/2010 | Travieso et al. |
| 2010/0049120 A1 | 2/2010 | Dijksman et al. |
| 2010/0101670 A1 | 4/2010 | Juncker et al. |
| 2010/0143448 A1 | 6/2010 | Nisato et al. |
| 2010/0222769 A1 | 9/2010 | Meng et al. |
| 2010/0234805 A1 | 9/2010 | Kaufmann et al. |
| 2010/0241103 A1 | 9/2010 | Kraft et al. |
| 2010/0292557 A1 | 11/2010 | Pesach et al. |
| 2010/0292635 A1 | 11/2010 | Sundar |
| 2010/0305550 A1 | 12/2010 | Meng et al. |
| 2011/0060280 A1 | 3/2011 | Caffey et al. |
| 2011/0144586 A1 | 6/2011 | Michaud et al. |
| 2011/0144617 A1 | 6/2011 | Meng et al. |
| 2011/0144619 A1 | 6/2011 | Meng et al. |
| 2011/0184342 A1 | 7/2011 | Pesach et al. |
| 2011/0190702 A1 | 8/2011 | Stumber |
| 2011/0202032 A1 | 8/2011 | Shih et al. |
| 2011/0270188 A1 | 11/2011 | Caffey et al. |
| 2011/0275987 A1 | 11/2011 | Caffey et al. |
| 2012/0016299 A1 | 1/2012 | Caffey |
| 2012/0041427 A1 | 2/2012 | Caffey et al. |
| 2012/0222488 A1 | 9/2012 | Slocum |
| 2012/0277733 A1 | 11/2012 | Pang et al. |
| 2012/0323218 A1 | 12/2012 | Pang et al. |
| 2013/0000119 A1 | 1/2013 | Tai et al. |
| 2013/0178792 A1 | 7/2013 | Li |
| 2013/0178826 A1 | 7/2013 | Li |
| 2013/0184640 A1 | 7/2013 | Li |
| 2013/0184641 A1 | 7/2013 | Li |
| 2013/0276974 A1 | 10/2013 | Pang et al. |
| 2013/0289497 A1 | 10/2013 | Humayun et al. |
| 2014/0074058 A1 | 3/2014 | Shih et al. |
| 2014/0074062 A1 | 3/2014 | Caffey et al. |
| 2014/0088554 A1 | 3/2014 | Li et al. |
| 2014/0088555 A1 | 3/2014 | Li et al. |
| 2014/0094770 A1 | 4/2014 | Li et al. |
| 2014/0094771 A1 | 4/2014 | Li et al. |

FOREIGN PATENT DOCUMENTS

| | | |
|---|---|---|
| DE | 3915708 A1 | 2/1990 |
| DE | 4436540 A1 | 4/1996 |
| DE | 102004036358 A1 | 2/2006 |
| EP | 209677 A1 | 1/1987 |
| EP | 0251680 A2 | 1/1988 |
| EP | 646381 A1 | 4/1995 |
| EP | 815896 A2 | 1/1998 |
| EP | 1649884 A1 | 4/2006 |
| EP | 1841491 A1 | 10/2007 |
| EP | 2298387 A1 | 3/2011 |
| EP | 2316505 A3 | 1/2012 |
| EP | 2473226 A1 | 7/2012 |
| EP | 2560703 A2 | 2/2013 |
| EP | 2242464 B1 | 5/2013 |
| EP | 2666510 A1 | 11/2013 |
| EP | 2319558 B1 | 5/2014 |
| EP | 2727616 A1 | 5/2014 |
| EP | 2323716 B1 | 3/2015 |
| GB | 1345764 A | 2/1974 |
| GB | 1452104 A | 10/1976 |
| IE | 38474 L | 6/1973 |
| JP | 56-500241 A | 3/1981 |
| JP | 3-41967 A | 2/1991 |
| JP | 2001-527220 A | 12/2001 |
| JP | 2002-143318 A | 5/2002 |
| JP | 2004-516949 A | 6/2004 |
| JP | 2014-97394 A | 5/2014 |
| JP | 2014-168703 A | 9/2014 |
| WO | 1984/001718 A1 | 5/1984 |
| WO | 1986/007269 A1 | 12/1986 |
| WO | WO-9513838 A1 | 5/1995 |
| WO | 1996/41159 A1 | 12/1996 |
| WO | WO-9917749 A1 | 4/1999 |
| WO | WO-9938552 A1 | 8/1999 |
| WO | WO-9962576 A1 | 12/1999 |
| WO | WO-200026367 A2 | 5/2000 |
| WO | WO-200040089 A1 | 7/2000 |
| WO | 00/74763 A2 | 12/2000 |
| WO | 2000/072900 A1 | 12/2000 |
| WO | 2000/074751 A1 | 12/2000 |
| WO | WO-0112158 A1 | 2/2001 |
| WO | 2001/21234 A1 | 3/2001 |
| WO | 2001/026706 A2 | 4/2001 |
| WO | WO-0156634 A1 | 8/2001 |
| WO | WO-0166173 A1 | 9/2001 |
| WO | WO-0194784 A1 | 12/2001 |
| WO | 2002/067688 A1 | 9/2002 |
| WO | WO-2003002170 A2 | 1/2003 |
| WO | 2003/009774 A2 | 2/2003 |
| WO | 2003/009784 A1 | 2/2003 |
| WO | WO-03024360 A1 | 3/2003 |
| WO | 2003/072193 A1 | 9/2003 |
| WO | 2004/002878 A2 | 1/2004 |
| WO | WO-2004014969 A1 | 2/2004 |
| WO | 2004/026281 A2 | 4/2004 |
| WO | 2004/067066 A1 | 8/2004 |
| WO | WO-2004066871 A2 | 8/2004 |
| WO | WO-2004073551 A2 | 9/2004 |
| WO | 2005/034814 A1 | 4/2005 |
| WO | WO-2005046769 A2 | 5/2005 |
| WO | WO-2006012280 A1 | 2/2006 |
| WO | WO-2006014793 A1 | 2/2006 |
| WO | 2006/022790 A1 | 3/2006 |
| WO | 2006/026768 A1 | 3/2006 |
| WO | 2006/060586 A1 | 6/2006 |
| WO | WO-2006075016 A1 | 7/2006 |
| WO | 2006/121921 A2 | 11/2006 |
| WO | 2007/035621 A2 | 11/2006 |
| WO | 2007/019539 A2 | 2/2007 |
| WO | WO-2007035621 A1 | 3/2007 |
| WO | 2007/065944 A1 | 6/2007 |
| WO | WO-2007084765 A2 | 7/2007 |
| WO | WO-2007106557 A2 | 9/2007 |
| WO | 2007/112328 A2 | 10/2007 |
| WO | 2007/125456 A2 | 11/2007 |
| WO | 2007/138590 A2 | 12/2007 |
| WO | 2008/024808 A2 | 2/2008 |
| WO | 2008/054788 A2 | 5/2008 |
| WO | 2008/139460 A2 | 11/2008 |
| WO | 2008/151667 A1 | 12/2008 |
| WO | 2009/015389 A2 | 1/2009 |
| WO | 2009/086112 A2 | 7/2009 |
| WO | 2009/137780 A2 | 11/2009 |
| WO | 2011/025913 A1 | 3/2011 |
| WO | 2011/028997 A1 | 3/2011 |
| WO | 2011/133724 A1 | 10/2011 |
| WO | 2011/133724 A3 | 1/2012 |
| WO | 2012/012406 A1 | 1/2012 |
| WO | 2013/075109 A3 | 10/2013 |
| WO | 2014/025796 A2 | 2/2014 |
| WO | 2014/025796 A3 | 2/2014 |
| WO | 2014/047638 A1 | 3/2014 |
| WO | 2014/047657 A2 | 3/2014 |

(56) References Cited

FOREIGN PATENT DOCUMENTS

OTHER PUBLICATIONS

"Krupin Eye Valve with Scleral Buckle, Krupin Eye Valve With Disk," Hood Laboratories Catalogue, F 079 Rev. Nov. 1992, 4 pages.
"The Optimed Advantage—Glaucoma Pressure Regulator," Optimed Advertising Brochure, Journal of Glaucoma, vol. 2, No. 3, 1993, 4 pages.
Chen et al. "Floating-Disk Parytene Micro Check Valve," Micro Electro Mechanical Systems, 2007, IEEE 20th International Conference on MEMS, Jan. 21-25, 2007, 4 pages.
Chen et al. "Floating-Disk Parylene Microvalve for Self-Regulating Biomedical Flow Controls," IEEE 21st International Conference on MEMS, 2008, Jan. 13-17, 2008, 4 pages.
Chen et al. "Surface-Micromachined Parylene Dual Valves for On-Chip Unpowered Microflow Regulation," Journal of Microelectromechanical Systems, vol. 16, No. 2, Apr. 2007, pp. 223-231.
Choudrhi et al. "A Comparison of Dorzolamide-Timolol Combination Versus the Concomitant Drugs," American Journal of Ophthalmology, Dec. 2000, 130, pp. 832-833.
Eliason et al. "An Ocular Perfusion System," Invent. Ophthalmol. Vis. Sci., vol. 19, No. 1, Jan. 1980, pp. 102-105.
Hashizoe et al. "Scleral Plug of Biodegradable Polymers for Controlled Release in the Vitreous" Arch Ophthalmol, vol. 112, Oct. 1994, pp. 1380-1384.
Jabs "Treatment of Cytomegalovirus Retinitis 0 1992," Arch Ophthlmol, vol. 110, Feb. 1992, pp. 185-187.
Khouri et al. "Use of Fixed-Dose Combination Drugs for the Treatment of Glaucoma," Drugs Aging, 2007, 24, 12, pp. 1007-1016.
Kimura et al. "A new Vitreal Dug Delivery System Using an Implantable Biodegradable Polymeric Device," Investigative Ophthalmology & Visual Science, May 1994, vol. 35, No. 6; pp. 2815-2819.
Lo et al. "A Refillable polymer Drug Delivery Device for reatment of Ocular Diseases," The Royal Society of Chemistry, Jan. 1, 2007, 28 pages.
Michelson et al. "Experimental Endophtalmitis Treated With an Implantable Osmotic Minipump," Arch Ophthalmol, vol. 97, Jul. 1979, pp. 1345-1346.
Miki, et al. "A Method for Chronic Drug Infusion Into the Eye," Japanese Journal of Opthalmology, vol. 28, 1984, pp. 140-146.
Pincus et al. "Why are Only 50% of Courses of Anti-Tumor Necrosis Factor Agents Continued for Only 2 Years in Some Settings? Need for Longterm Observations in Standard Care to Compliment Clinical Trials," Journal of Rheumatology, 2006, 33, 12, pp. 2372-2375.
Pope et al. "MRI in Patients with High-Grade Gliomas Treated with Bevacizumab and Chemotherapy," Neurology, 2006, 66, pp. 1258-1260.
Rubsamen et al. "Prevention of Experimental Proliferative Vitreoretinopathy With a Biodegradable Intravitreal Implant for the Sustained Release of Fluorouracil," Arch Ophthalmol, vol. 112, Mar. 1994, pp. 407-413.
Sanborn et al. "Sustained-Release Ganciclovir Therapy for Treatment of Cytomegalovirus Retinitis," Arch Ophthmol, vol. 110, Feb. 1992; pp. 188-195.
Smith et al. "Intravitreal Sustained-Release Ganiclovir," Arch Ophthlmol, vol. 110, Feb. 1992, pp. 255-258.
Stark-Vance, "Bevacizumab and CPT-11 in the Treatment of Relapsed Malignant Glioma," Abstract from the World Federation of Neuro-Oncology Second Quadrennial Meeting and Sixth Meeting of the European Association for Neuro-Oncology, May 5-8, 2005, Abstract 342, p. 369.
Steyer "Alcon Eye-Drug Setback Raises the Stakes," The Street. Com, Oct. 14, 2004, 4 pages.
Strohmaier et al. "The Efficacy and Safety of the Dorzolamide—Timolol Combination Versus the Concomitant Administration of its Components," Ophthalmology, Oct. 1998, vol. 105, No. 10, pp. 1936-1944.
Xie et al. "An Electrochemical Pumping System for On-Chip Gradient Generation," Analytical Chemistry, 8 pages (A-H).
Examination Report for European Patent Application No. 07753177.0, dated Jan. 29, 2009, 6 pages.
Invitation to Pay Additional Fees and Partial International Search for PCT Application No. PCT/US2007/006530, dated Jul. 31, 2007, 7 pages.
International Search Report for PCT Application No. PCT/US2007/006530, dated Nov. 12, 2007, 7 pages.
Written Opinion for PCT Application No. PCT/US2007/006530, dated Nov. 12, 2007, 10 pages.
Invitation to Pay Additional Fees and Partical International Search for PCT Application No. PCT/US2009/030019, dated Jun. 5, 2009, 5 pages.
International Search Report for PCT Application No. PCT/US2009/030019, dated Jul. 20, 2009, 7 pages.
Written Opinion for PCT Application No. PCT/US2009/030019, dated Jul. 20, 2009, 9 pages.
Invitation to Pay Additional Fees and Partial International Search for PCT Application No. PCT/US2008/087690, dated May 15, 2009, 5 pages.
International Search Report for PCT Application No. PCT/US2008/087690, dated Aug. 11, 2009, 7 pages.
Written Opinion for PCT Application No. PCT/US2008/087690, dated Aug. 11, 2009, 10 pages.
Invitation to pay Additional Fees and Partial International Search for PCT Application No. PCT/US2009/043317, dated Nov. 16, 2009, 5 pages.
Invitation to Pay Additional Fees and Partial International Search for PCT Application No. PCT/US2009/043313, dated Nov. 16, 2009, 5 pages.
International Search Report for PCT Application No. PCT/US2009/043325, dated Dec. 11, 2009, 9 pages.
Written Opinion for PCT Application No. PCT/US2009/043325, dated Dec. 11, 2009, 9 pages.
Examination Report for European Patent Application No. 07753177.0, dated Feb. 5, 2010, 3 pages.
International Search Report for PCT Application No. PCT/US2009/043317, dated Feb. 16, 2010, 7 pages.
Written Opinion for PCT Application No. PCT/US2009/043317, dated Feb. 16, 2010, 8 pages.
International Search Report for PCT Application No. PCT/US2009/043313, dated Feb. 25, 2010, 8 pages.
Written Opinion for PCT Application No. PCT/US2009/043313, dated Feb. 25, 2010, 8 pages.
Japanese Office Action dated Apr. 9, 2013 for corresponding Japanese Patent Application No. 2010-539,873, English translation of "Notification of Reason for Rejection", 6 pages.
Examination Report Received for European Patent Application No. 11153615.7 dated Oct. 24, 2012, 4 pages.
Examination Report Received for Japanese Patent Application No. 2011-508709 dated Mar. 4, 2014, 5 pages (3 pages of English Translation and 2 pages of Office Action).
Examination Report Received for Chinese Patent Application No. 2009801265492, dated Apr. 28, 2014, 8 pages (5 pages of English Translation and 3 pages of Office Action).
Examination Report Received for Japanese Patent Application No. 2013-242517 dated Nov. 25, 2014, 4 pages (Official copy only) (including 1 page of reference record) (In accordance with 37 CFR § 1.98(a) (3)).
Examination Report Received for Mexican Patent Application No. MX/A/2013/013831 dated Feb. 20, 2014, 1 page.
PCT International Patent Application No. PCT/US2010/045897, International Search Report and Written Opinion dated Dec. 28, 2010, 12 pages.
PCT International Patent Application No. PCT/US2013/061494, Invitation to Pay Additional Fees and Partial International Search, dated Jan. 28, 2014, 6 pages.

(56) References Cited

OTHER PUBLICATIONS

Examination Report Received for Australian Patent Application No. 2010284216 dated Mar. 20, 2014, 5 pages.
PCT International Patent Application No. PCT/US2010/047811, International Preliminary Report on Patentability dated Mar. 6, 2012, 15 pages.
PCT International Patent Application No. PCT/US2011/033329, International Preliminary Report on Patentability dated Nov. 1, 2012, 13 pages.
PCT International Patent Application No. PCT/US2013/053812, International Preliminary Report on Patentability dated Feb. 10, 2015, 11 pages.
Extended Search Report issued for European Patent Application No. 11153615.7, dated Dec. 15, 2011, 8 pages.
Examination Report in European Patent Application No. 11153618.1, dated Oct. 14, 2013, 5 pages.
Extended Search Report issued for European Patent Application No. 11153618.1, dated Dec. 12, 2011, 9 pages.
Extended Search Report issued for European Patent Application No. 13168508.3, dated Oct. 24, 2013, 7 pages.
Examination Report in Mexican Patent Application No. MX/a/2008/011714, dated Jan. 19, 2012.
International Application Serial No. PCT/US2010/047811, Invitation to Pay Additional Fees and Partial Search Report dated Dec. 2, 2010, 8 pages.
International Application No. PCT/US2011/033329, International Search Report and Written Opinion dated Nov. 23, 2011, 16 pages.
International Application No. PCT/US2011/033329, Invitation to Pay Additional Fees and Partial Search Report, dated Aug. 4, 2011, 5 pages.
International Application Serial No. PCT/US2011/044508, International Search Report and Written Opinion dated Dec. 1, 2011, 11 pages.
Examination Report Received for European Patent Application No. 11153618.1, dated Oct. 23, 2012, 5 pages.
Examination Report Received for Chinese Patent Application No. 2009801265562, dated Oct. 10, 2014, 6 pages (1 page of English Translation and 4 pages of Official Copy).
Examination Report Received for European Patent Application No. 10008072.0, dated Jun. 17, 2013, 6 pages.
Notice of Allowance Received for Canadian Patent Application No. 2,647,362, dated Feb. 5, 2014, 1 page.
Examination Report Received for Chinese Patent Application No. 2011800303418, dated Jul. 2, 2014, 15 pages. (8 pages of English Translation and 7 pages of Official Copy).
Examination Report Received for Canadian Patent Application No. 2,833,354, dated Sep. 3, 2014, 2 pages.
Examination Report Received for Chinese Patent Application No. 2009801265562, dated Mar. 20, 2014, 8 pages. (5 pages of English Translation and 3 pages of Official Copy).
Extended European Search Report Received for EP Patent Application No. 14152346.4, dated Apr. 9, 2014, 6 pages.
Examination Report Received for Japanese Patent Application No. 2009-500481, dated Sep. 9, 2014, 1 page (Official Copy Only).
Examination Report Received for Japanese Patent Application No. 2009-500481, dated Mar. 28, 2014, 2 pages (Official Copy Only).
Examination Report Received for Japanese Patent Application No. 2010-539873, dated Apr. 8, 2014, 2 pages. (1 page of Translation and 1 page of Official Copy).
PCT International Application No. PCT/US2013/053812, International Search Report dated Sep. 4, 2014, 6 pages.

* cited by examiner

APPARATUS AND METHODS FOR DELIVERING THERAPEUTIC AGENTS

CROSS-REFERENCE TO RELATED APPLICATIONS

This application is a divisional application of, and incorporates herein by reference in its entirety, U.S. patent application Ser. No. 12/340,095, filed on Dec. 19, 2008, which claims priority to and the benefit of, and incorporates herein by reference in their entireties, U.S. Provisional Patent Application No. 61/015,509, which was filed on Dec. 20, 2007, and U.S. Provisional Patent Application No. 61/197,750, which was filed on Oct. 30, 2008.

TECHNICAL FIELD

In various embodiments, the invention relates to apparatus and methods for delivering therapeutic agents to a patient's body part, such as, for example, to a patient's eye.

BACKGROUND

Medical treatment often requires the administration of a therapeutic agent (e.g., medicament, drugs, etc.) to a particular part of a patient's body. Intravenous injection has long been a mainstay in medical practice to deliver drugs systemically. Some maladies, however, require administration of drugs to anatomical regions to which access is more difficult to achieve.

A patient's eye is a prime example of a difficult-to-reach anatomical region. Ocular pathologies, such as diabetic retinopathy and macular degeneration, are typically treated by administration of drugs to the vitreous humor, which has no fluid communication with the vasculature. Such administration not only delivers the drug directly to where it is needed, but also minimizes the exposure of the rest of the patient's body to the drug and, therefore, to its potential side effects.

Injection of drug into the patient's body (e.g., into the vitreous humor of the eye), while medically feasible, typically delivers a bolus of the drug. Bolus injections may, however, present several problems. First, their use in treating chronic eye conditions typically necessitates repeated injections into the eye, a painful procedure that generally requires repeated and expensive visits to a physician's office, and can cause trauma to the eye. Second, because a bolus injection intrinsically produces a sawtooth-profile dependence of drug concentration over time, the dosage of the injection tends to be near the threshold limit of toxicity. Injection of such dosages typically increases the likelihood of systemic side effects, as occurs, for example, with ranibizumab.

A need therefore exists for apparatus and methods of administering appropriately chosen therapeutic drugs to the eye so that the time variation of the concentrations of those drugs in the eye is minimized.

SUMMARY OF THE INVENTION

In various embodiments, the present invention features apparatus and methods for delivering therapeutic agents to a patient's body part, such as, for example, to a patient's eye. In one approach, a drug-delivery device features a single reservoir for delivering one of a variety of therapeutic agents to the patient. In another approach, the drug-delivery device features multiple reservoirs for delivering more than one different therapeutic agent to the patient, for example in a staged or alternating fashion.

Accordingly, in one aspect, embodiments of the invention feature a drug-delivery device that includes a first reservoir for containing a first liquid having a first therapeutic agent, a second reservoir for containing a second liquid having a second therapeutic agent different from the first therapeutic agent, and at least one cannula in fluid communication with the first and second reservoirs (e.g., a first cannula in fluid communication with the first reservoir and a second, separate cannula in fluid communication with the second reservoir). The at least one cannula may have an outlet for separately delivering the first and second liquids to the patient. In various embodiments, the first reservoir in fact includes the first liquid and the second reservoir includes the second liquid.

In general, in another aspect, embodiments of the invention feature a method for treating an ophthalmic condition. The method includes providing a drug-delivery device as just described, attaching the drug-delivery device onto the conjunctiva of a patient's eye such that the outlet of the at least one cannula penetrates the conjunctiva, filling the first reservoir with the first liquid having the first therapeutic agent, filling the second reservoir with the second liquid having the second therapeutic agent (which is different from the first therapeutic agent), and separately delivering the first and second therapeutic agents to the patient via the outlet of the at least one cannula.

In various embodiments, each of the first and second therapeutic agents treats glaucoma and/or ocular hypertension. In such a case, the first and second therapeutic agents may each be selected from the group consisting of acetazolamide, betaxolol, bimatoprost, brimonidine, brinzolamide, carbidopa, carteolol, dorzolamide, epinephrine, latanoprost, levodopa, levobunolol, levobetaxolol, loratadine, metipranolol, pilocarpine, pseudoephedrine, timolol, travoprost, and unoprostone isopropyl. In another embodiment, the first and second therapeutic agents treat age-related macular degeneration, macular edema associated with diabetic retinopathy, and/or macular edema associated with retinovascular occlusive diseases. In this case, the first and second therapeutic agents may be selected from the group consisting of ranibizumab, pegaptanib, verteporfin, bevacizumab, a steroid, a drug that prevents beta amyloid deposition in the retina, an anti-human complement activation blocker that blocks complement H activation in the eye, and small interfering RNA (siRNA) molecules. In yet another embodiment, each of the first and second therapeutic agents treat cytomegalovirus retinitis and may be selected from the group consisting of valganciclovir, vitravene, and cidofovir. In still another embodiment, each of the first and second therapeutic agents treat itching and allergic conjunctivitis and may be selected from the group consisting of loteprednol etabonate, naphazoline, pheniramine maleate, pemirolast, and ketotifen fumarate.

In an alternative embodiment, the first and second therapeutic agents are chosen so as to treat two different maladies selected from the group consisting of glaucoma, ocular hypertension, age-related macular degeneration, macular edema associated with diabetic retinopathy, macular edema associated with retinovascular occlusive diseases, low tear production, cytomegalovirus retinitis, bacterial conjunctivitis, itching and allergic conjunctivitis, post-operative eye inflammation, inflammation of the cornea due to herpes simplex virus, postoperative inflammation after cataract extraction, corneal ulcers, and Sjögren's syndrome.

In another embodiment of the drug-delivery device, each of the first and second therapeutic agents treats recurrent malignant glioma and/or malignant brain tumors. In such a case, the first and second therapeutic agents may each be selected from the group consisting of bevacizumab, irinotecan, and a steroid. In yet another embodiment, each of the first and second therapeutic agents suppresses an inflammatory reaction. In this case, the first therapeutic agent may be a steroid and the second therapeutic agent may be either a non-steroidal drug or an anti-cancer drug. In still another embodiment, each of the first and second therapeutic agents provides neuroprotection for a retinal disease, glaucoma, and/or a brain disorder. For example, each of the first and second therapeutic agents is selected from the group consisting of a brain derived growth factor, a ciliary neurotrophic factor, a basic fibroblast growth factor, a nerve growth factor, and a tumor necrosis growth factor inhibitor.

In an alternative embodiment, the first and second therapeutic agents are chosen so as to treat two different maladies selected from the group consisting of recurrent malignant glioma, a malignant brain tumor, alzheimers, cerebral edema, and an inflammatory reaction.

In general, in yet another aspect, embodiments of the invention feature a drug-delivery device that includes a reservoir and a cannula in fluid communication with the reservoir. The reservoir contains a liquid that includes a therapeutic agent, and the cannula has an outlet for delivering the therapeutic agent to a patient.

In general, in still another aspect, embodiments of the invention feature a method for treating an ophthalmic condition. The method includes implanting a drug-delivery device in a patient's eye and filling the drug-delivery device with a liquid that includes a therapeutic agent.

In various embodiments of each of these latter two aspects, the therapeutic agent is selected from the group consisting of acetazolamide, betaxolol, bevacizumab, bimatoprost, brimonidine, brinzolamide, carbidopa, carteolol, cidofovir, cyclosporine, dorzolamide, epinephrine, a growth factor, irinotecan, ketorolac tromethamine, ketotifen fumarate, latanoprost, levobetaxolol, levobunolol, levodopa, levofloxacin, loratadine, loteprednol etabonate, metipranolol, naphazoline, ofloxacin, pegaptanib, pemirolast, pheniramine maleate, pilocarpine, pseudoephedrine, ranibizumab, a steroid, timolol, travoprost, trifluridine, tumor necrosis factor blocker, unoprostone isopropyl, valganciclovir, verteporfin, vitravene, a drug that prevents beta amyloid deposition in the retina or in the brain, an anti-human complement activation blocker that blocks complement H activation in the eye, and siRNA molecules.

In general, in a further aspect, embodiments of the invention feature a method for treating a cancerous condition. The method includes implanting a drug-delivery device near a patient's tumor and filling the drug-delivery device with a combination of drugs. The combination of drugs may be, for example, one of the following: i) bevacizumab and CPT-11; ii) ranibizumab and CPT-11; iii) letrozole and tamoxifen; iv) doxorubicin and docetaxel; v) bevacizumab and any chemotherapy drug; vi) gemcitabine and CP-870,893; vii) PF-3512676 and a cytotoxic chemotherapy drug; viii) bevacizumab and paclitaxel; ix) docetaxel and sunitinib; x) bevacizumab and sunitinib; xi) lapatinib and letrozole; xii) ixabepilone and capecitabine; and xiii) paclitaxel protein-bound and a taxane.

In general, in an additional aspect, embodiments of the invention feature a drug-delivery device that includes a first reservoir for containing a first liquid having a first therapeutic agent, a second reservoir for containing a second liquid having a second therapeutic agent different from the first therapeutic agent, memory for storing a drug-delivery regimen, and a microprocessor for controlling a delivery of the first and second liquids to a patient through at least one cannula based on an execution of the stored drug-delivery regimen.

In various embodiments, the drug-delivery device also includes a sensor for receiving feedback from the patient and/or a receiver for receiving wireless instructions (e.g., from a physician) that reprogram the drug-delivery regimen. The microprocessor may also modify the drug-delivery regimen based on the feedback. The feedback may be, for example, a measured eye pressure for the patient, a position of the patient, an activity being undertaken by the patient, and/or a measured residual amount of the first or second therapeutic agent present in a patient's tissue. In addition, execution of the drug-delivery regimen may be impacted by a variable such as the time of day, a patient-specific factor, and/or identities of the first and second therapeutic agents.

These and other objects, along with advantages and features of the embodiments of the present invention herein disclosed, will become more apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DESCRIPTION

In general, embodiments of the present invention pertain to apparatus and methods for delivering therapeutic agents to a patient's body part, such as, for example, to the patient's eye. In certain embodiments, the implantable drug-delivery device for the eye combines small size and a refillable reservoir. The small size minimizes discomfort from the device to the patient's eye, while the refillable reservoir allows the device to be refilled in situ, rather than being replaced. As such, a fluid, such as a solution of a drug, can be supplied to the patient's eye over extended periods of time.

In certain embodiments, the drug-delivery device includes the refillable reservoir, a cannula, and a valve. The refillable reservoir holds the fluid to be delivered, the cannula directs the fluid to the targeted site, and the valve controls the delivery of the fluid and prevents backflow. In one embodiment, the refillable reservoir has a self-resealing upper layer that can be pierced with a needle for refilling, and a lower layer that resists needle punctures and thereby protects the eye from accidental injury during the refilling process. For its part, the cannula may be tapered to facilitate its insertion into the patient's eye.

Figure 1A:
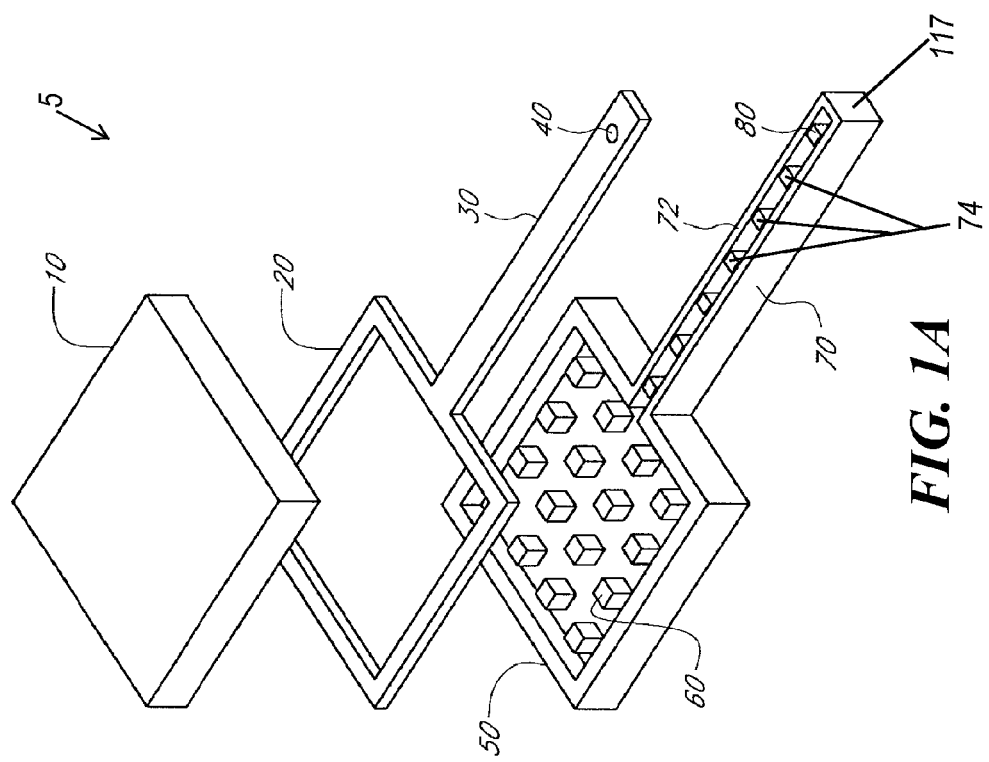
FIG. 1A is an exploded view of a drug-delivery device in accordance with one embodiment of the invention.
Figure 1B:
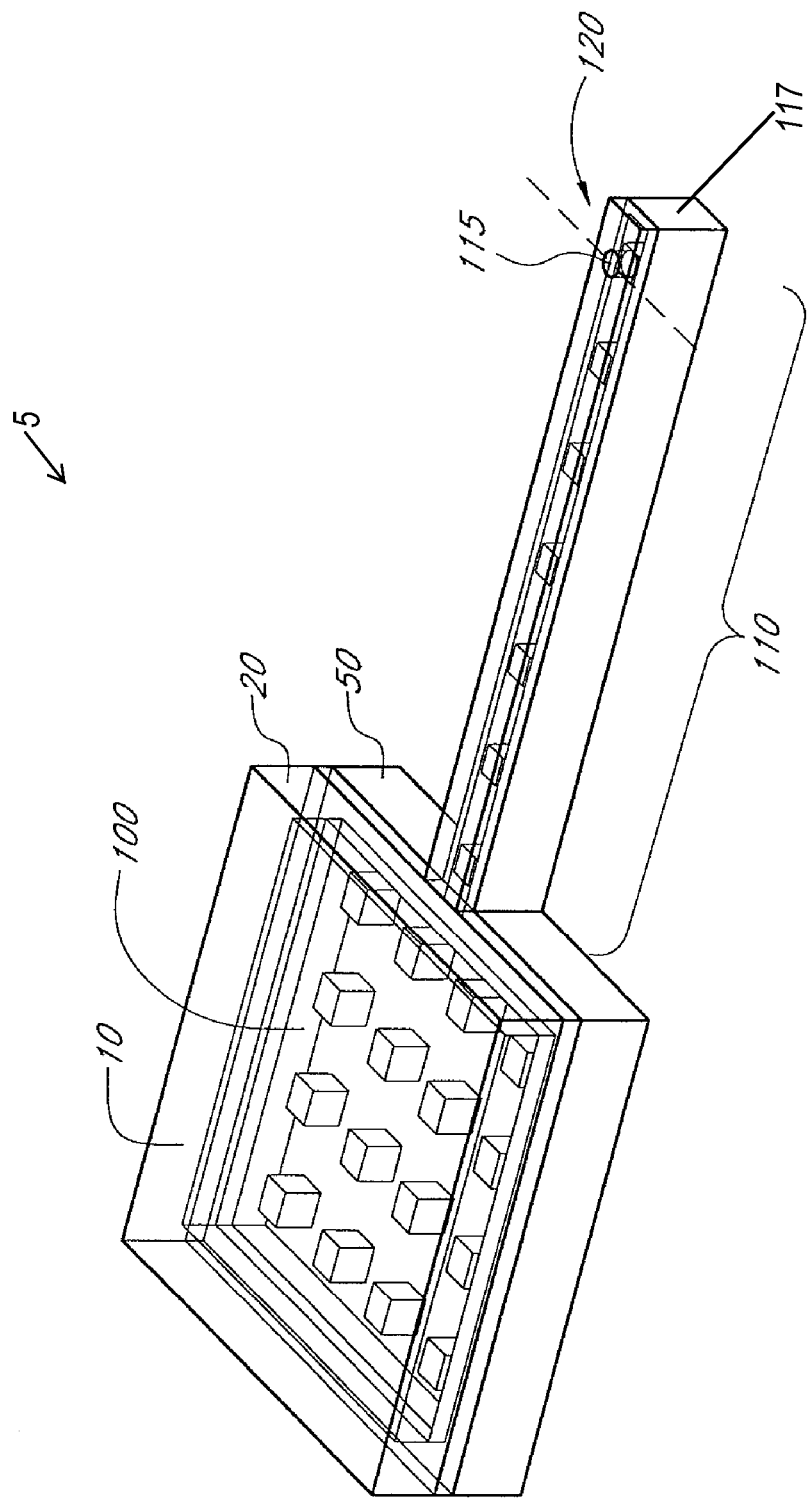
FIG. 1B is an assembled view of the exemplary drug-delivery device depicted in FIG. 1A.

FIGS. 1A and 1B schematically illustrate an exploded view and an assembled view, respectively, of one embodiment of a drug-delivery device 5. The device 5 includes a reservoir 100 that is configured to contain a liquid comprising a therapeutic agent (e.g., a drug), and a cannula 110 that is in fluid communication with the reservoir 100. At or near its distal end 117, the cannula 110, which is configured for insertion into a patient (e.g., into a patient's eye), includes an outlet 115 for delivering the drug to the patient. In addition, as described further below, the drug-delivery device 5 may also include a valve 120 positioned at or near the distal end 117 of the cannula 110. Alternatively, the valve 120 may be positioned elsewhere along the length of the cannula 110, such as at its end proximal the reservoir 100.

In one embodiment, the reservoir 100 is a refillable multi-layered structure having a first wall 10 that is puncturable by a needle and a second, opposite wall 50 that is generally unpuncturable by the needle. As explained further below, the needle is used in refilling the reservoir 100 with a liquid comprising a therapeutic agent, such as a drug. The first wall 10 may include a pliable, drug-impermeable polymer (e.g., silicone) layer that does not leak after being pierced by a needle, while the second wall 50 may include a layer having a less pliable and more mechanically robust material (e.g., a stiffer material, such as a polymer or a composite). Alternatively, the second wall 50 may include a greater thickness of the same material used to fabricate the first wall 10. In certain embodiments in which the drug-delivery device 5 is implanted in or on a patient's eye, the second wall 50 is placed adjacent to the sclera of the eye, and the greater mechanical strength of the second wall 50 limits the stroke of the needle used to puncture the first wall 10 to refill the reservoir 100. In this fashion, the eye is protected from accidental punctures. The reservoir 100 may be formed by bonding the first wall 10 and the second wall 50 either to each other or to one or more intervening layers 20, as described more fully below.

In one embodiment, the reservoir 100 includes integral mechanical support structures 60 that reduce the possible contact area between the first wall 10 and the second wall 50 and that prevent the reservoir 100 from collapsing completely. The mechanical support structures 60 may be, or include, one or more protrusions (e.g., posts) extending from at least one of the first wall 10 and the second wall 50. Other mechanical support structures are also compatible with various embodiments described herein.

In one embodiment, the cannula 110 includes an elongate first portion 70 and a wall 30 that together define a lumen 72 through the cannula 110. The cannula 110 may also include one or more integral mechanical support structures 74 in the lumen 72 to prevent the cannula 110 from collapsing and occluding the lumen 72. For example, the mechanical support structures 74 may be, or include, one or more protrusions (e.g., posts) extending from an inner surface of the first portion 70 of the cannula 110 towards the wall 30 of the cannula 110. In certain embodiments, the mechanical support structures 74 have a height that extends from the inner surface of the first portion 70 to the wall 30 and a width that extends less than the full width of the lumen 72. Other mechanical support structures are also compatible with various embodiments described herein.

The end 117 of the cannula 110 may be configured to be inserted into a patient's eye. For example, the end 117 of the cannula 110 may be tapered to facilitate insertion into the eye. In certain other embodiments, the end 117 has rounded corners that facilitate insertion into the eye. In one embodiment, the outer diameter of the cannula 110 is less than or equal to the outer diameter of a 25-gauge needle. In another embodiment, the outer diameter of the cannula 110 is less than 1 millimeter (e.g., 0.5 millimeters). In embodiments in which the drug-delivery device 5 is implantable in, or on, the eye, the outer diameter of the cannula 110 is sufficiently small to obviate the need for sutures at the insertion site to help maintain the integrity of the eye.

The cannula 110 may also include one or more flow-regulator structures (e.g., valves) to maintain a constant flow rate. In this way, the administered dosage of a drug depends on the duration that fluid containing the drug flows through the cannula 110, rather than on the magnitude of an applied pressure that drives fluid flow through the cannula 110. More accurate control of the administered dosage may thereby be obtained, and the dosage remains independent of external mechanical influence (e.g., if the patient rubs his or her eye). Instead of, or in addition to, the one or more flow-regulator structures of the cannula 110, the reservoir 100 may include one or more such flow-regulator structures.

In addition, the cannula 110 may include one or more fluid-flow isolation structures (e.g., valves) that isolate the reservoir 100 from a patient's body (e.g., the eye) during various operations that involve the reservoir 100 (e.g., purging, cleaning, and/or refilling), thereby preventing the exchange of fluid (in either direction) between the reservoir 100 and the patient's body. Instead of, or in addition to, the one or more fluid-flow isolation structures of the cannula 110, the reservoir 100 may include one or more such fluid-flow isolation structures.

Figure 2:
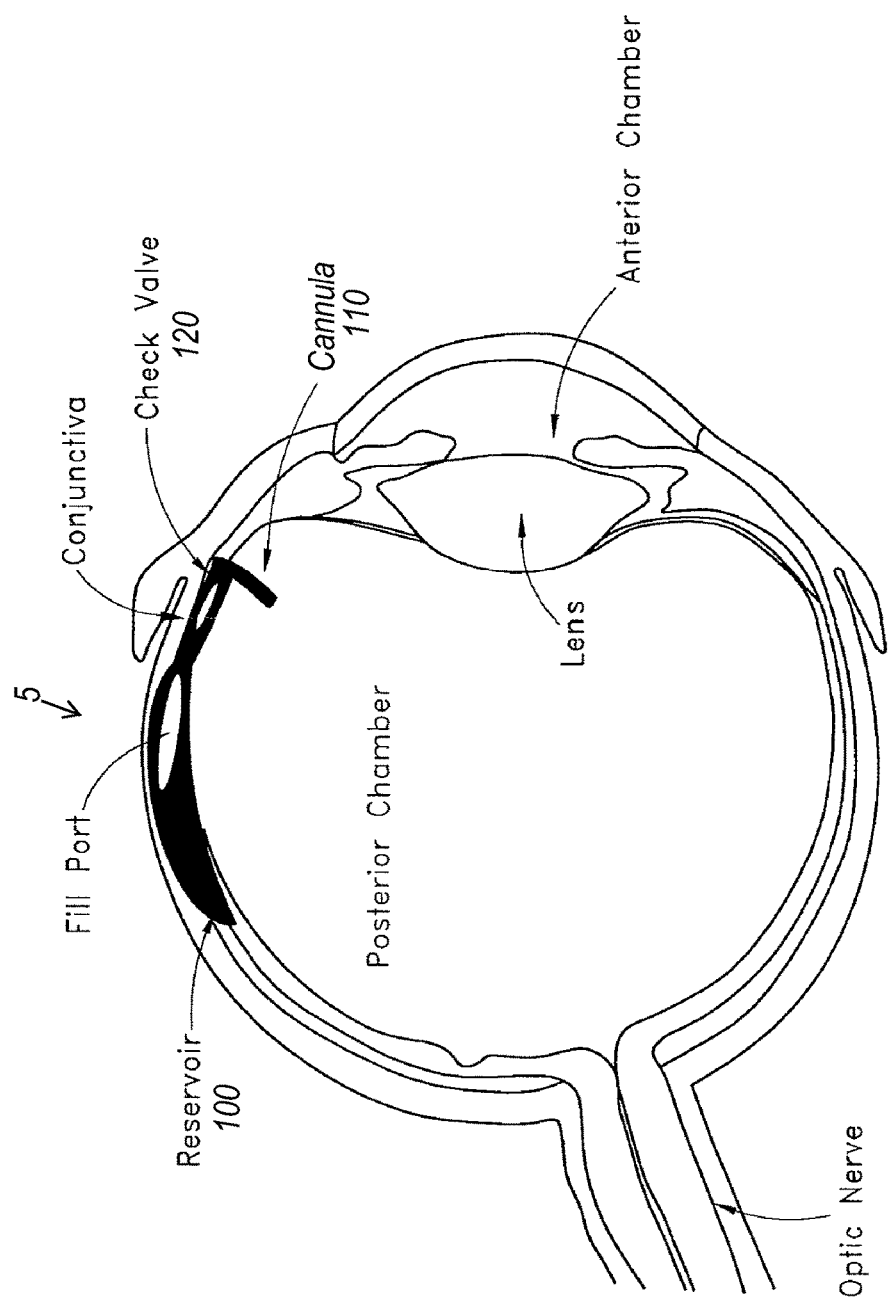
FIG. 2 illustrates a drug-delivery device implanted in a patient's eye in accordance with one embodiment of the invention.

FIG. 2 schematically illustrates the exemplary drug-delivery device 5 implanted in the eye of a patient in accordance with one embodiment of the invention. As illustrated, the device 5 is placed upon the conjunctiva of the eye, and cannula 110 is inserted therethrough in to the posterior chamber of the eye. As described more fully below, in certain embodiments, the reservoir 100 includes a needle-pierceable portion in the first wall 10 that serves as a fill port for the reservoir 100. The drug-delivery device 5 administers fluid to the posterior chamber of the eye through the cannula 110 and the valve 120. In other embodiments, the device 5 is used to administer fluid to the anterior chamber of the eye, which is separated from the posterior chamber by the lens.

The device 5 may also be implanted in other portions of the body. For example, the device 5 may be implanted in the sub-arachnoid space of the brain to provide chemotherapy or to provide another type of treatment for the brain as described below, near a tumor in any portion of the patient's body to provide chemotherapy, or in a pancreas that does not respond well to glucose to provide agents (e.g., proteins, viral vectors, etc.) that will trigger insulin release.

As mentioned, in one embodiment, the drug-delivery device 5 is refillable. With reference again to FIG. 1A, the first wall 10 of the reservoir 100 may be puncturable by a needle (not shown), thereby allowing the reservoir 100 to be refilled through the needle. In one embodiment, at least a portion of the first wall 10 is self-sealing. For example, a self-sealing portion may include a soft plastic material that can be punctured with the needle and that reseals itself upon removal of the needle. In one embodiment, the self-sealing material advantageously provides a reservoir refill site that can withstand multiple punctures, and is biocompatible. Examples of materials that may be employed for the self-sealing material include, but are not limited to, PDMS, parylene C, parylene HT, polycarbonates, polyolefins, polyurethanes, copolymers of acrylonitrile, copolymers of polyvinyl chloride, polyamides, polysulphones, polystyrenes, polyvinyl fluorides, polyvinyl alcohols, polyvinyl esters, polyvinyl butyrate, polyvinyl acetate, polyvinylidene chlorides, polyvinylidene fluorides, polyimides, polyisoprene, polyisobutylene, polybutadiene, polyethylene, polyethers, polytetrafluoroethylene, polychloroethers, polymethylmethacrylate, polybutylmethacrylate, polyvinyl acetate, nylons, cellulose, gelatin, silicone rubbers and porous rubbers. Where the self-sealing material includes a plastic that is capable of leaching or absorbing drugs that come into contact with it (e.g., silicone), parylene may be coated over the plastic so that less drug is exposed to the plastic.

To illustrate the stability of PDMS as a material for the first wall 10, three different needle styles were inserted into a slab of PDMS: (i) a 20-gauge standard sharp-tipped needle, (ii) a 30-gauge non-coring needle, and (iii) a 30-gauge coring needle. The puncture sites were then observed using scanning electron microscopy and optical microscopy. The 20-gauge standard sharp-tipped needle and the 30-gauge non-coring needle allowed the PDMS to self-seal the puncture hole after the needle was removed. However, the 30-gauge coring needle left a channel in the PDMS after it was removed. The puncture mechanism in small-diameter needles of either standard or non-coring styles appears to tear and displace the PDMS material rather than removing material, thereby allowing the PDMS to reseal the puncture hole. In addition, the structural integrity of the PDMS was observed after multiple punctures with a 25-gauge needle. Table 1 shows the relationship between the thickness of the wall 70 and leakage for tests performed under atmospheric conditions with leakage determined through visual inspection.

TABLE 1

| Wall Thickness (millimeters) | Number of Punctures Until Failure |
|---|---|
| 0.3557 | 1 |
| 0.5080 | 7 |
| 0.4826 | 10 |
| 0.4578 | 22 |
| 0.5334 | 21 |

The refillable reservoir 100 may be used with a variety of drug-containing fluids, depending upon the type of malady being treated. Typically, the pharmaceuticals chosen for eye treatment will penetrate the protective physiological barriers of the eye such as the cornea, sclera, and the blood-retina barrier. In addition, the pharmaceuticals will target difficult-to-reach intraocular tissues such as the ciliary body, retina, and angle. As examples, fluids containing the following therapeutic agents, either alone or in proper combination, may be used with the drug-delivery devices described herein for the treatment of the following maladies:

i) acetazolamide, betaxolol, bimatoprost, brimonidine, brinzolamide, carbidopa, carteolol, dorzolamide, epinephrine, latanoprost, levodopa, levobunolol, levobetaxolol, loratadine, metipranolol, pilocarpine, pseudoephedrine, timolol, travoprost, and unoprostone isopropyl for the treatment of glaucoma and/or ocular hypertension;

ii) ranibizumab, pegaptanib, verteporfin, bevacizumab (e.g., Avastin®), steroids (such as fluocinolone and triamcinolone (e.g., Kenalog®)), drugs that prevent beta amyloid deposition in the retina (such as tarenflurbil (e.g., Flurizan®), anti-human complement activation blockers to block complement H activation in the eye, and siRNA molecules (the delivery of which may be appropriately titrated) for the treatment of age-related macular degeneration and/or the macular edema associated with diabetic retinopathy and retinovascular occlusive diseases;

iii) cyclosporine ophthalmic emulsion for the treatment of low tear production;

iv) valganciclovir, vitravene, and cidofovir for the treatment of cytomegalovirus retinitis;

v) levofloxacin for the treatment of bacterial conjunctivitis;

vi) loteprednol etabonate, naphazoline, pheniramine maleate, pemirolast, and ketotifen fumarate for the treatment of itching and allergic conjunctivitis;

vii) loteprednol etabonate for the treatment of post-operative eye inflammation;

viii) trifluridine for the treatment of inflammation of the cornea in children due to herpes simplex virus;

ix) ketorolac tromethamine for the treatment of postoperative inflammation after cataract extraction;

x) ofloxacin for the treatment of corneal ulcers;
xi) pilocarpine for the treatment of Sjögren's syndrome, an autoimmune disorder;
xii) bevacizumab (e.g., Avastin®), irinotecan (also known as CPT-11), and steroids for the treatment of adult patients having recurrent malignant glioma and/or for the treatment of pediatric patients having high risk malignant brain tumors;
xiii) drugs that prevent beta amyloid deposition in the brain (such as tarenflurbil (e.g., Flurizan®) for the treatment of alzheimers;
xiv) steroids to reduce edema following a central nervous system stroke and/or to reduce cerebral edema following head trauma;
xv) steroids in combination with non-steroidal drugs, or steroids in combination with anti-cancer drugs (e.g., tumor necrosis factor blocker), to suppress inflammatory reactions (e.g., macrophages); and
xvi) growth factors, such as brain derived growth factor, ciliary neurotrophic factor, basic fibroblast growth factor, and nerve growth factor, and tumor necrosis growth factor inhibitor for neuroprotection in retinal diseases, glaucoma, and/or brain disorders.

Because the refillable reservoir 100 can be used with a variety of different drug containing fluids, it may be, in some cases, desirable to remove any remaining fluid from the reservoir 100 before refilling. Remaining fluid in the reservoir 100 may be removed therefrom by, for example, inserting a needle or syringe through the self-sealing portion of the first wall 10 to suck out the fluid from the reservoir 100. Then, the reservoir 100 may be refilled with a new drug-containing fluid via another needle or syringe inserted through the self-sealing portion of the first wall 10. Purging, if desired, can be effected through repeated cycles of injection and removal of a purging fluid.

In one embodiment, the refillability of the reservoir 100 allows the drug-delivery device 5 to be smaller than it may otherwise be because the reservoir 100 need not be sufficiently large to hold a lifetime supply of the drug to be administered. The smaller size of the drug-delivery device 5 advantageously reduces the invasiveness of the device 5 both for implantation and daily use.

In addition, the refillability of the reservoir 100 may advantageously allow a physician to tailor a therapeutic regimen to a patient's changing needs or to take advantage of new advances in medicine. In one embodiment, the refillable reservoir 100 stores at least a one-month supply of the drug (e.g., a six-month supply) to reduce the number of refills required.

Figure 3:
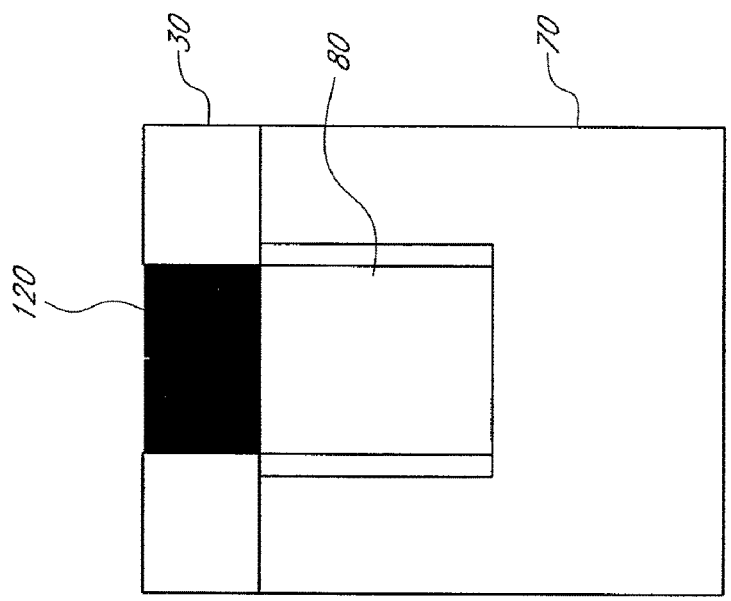
FIG. 3 is a cross-sectional view of a portion of the exemplary drug-delivery device depicted in FIG. 1B.
Figure 4A:
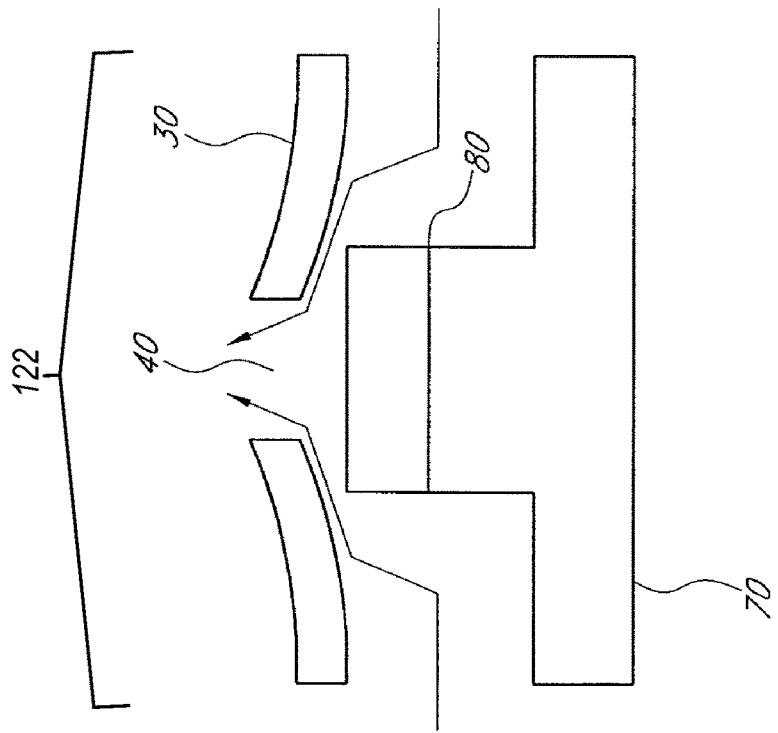
FIGS. 4A and 4B are cross-sectional views illustrating the operation of a valve for a drug-delivery device in accordance with one embodiment of the invention.
Figure 4B:
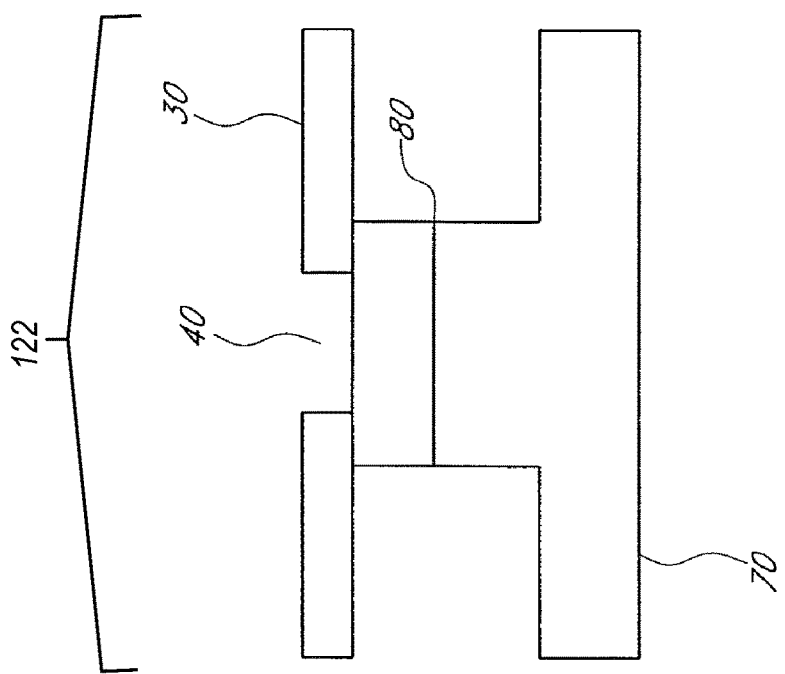

FIG. 3 schematically illustrates a cross-sectional view of one embodiment of the valve 120 at the distal end 117 of the cannula 110. The cross-sectional view of FIG. 3 is in the plane indicated by the dashed line of FIG. 1B. The valve 120 may include a valve seat 80 and an element movable between first and second positions. FIGS. 4A and 4B schematically illustrate cross-sectional views of the valve 120 with a movable element 122 in the first and second positions, respectively. In one embodiment, a flexible portion of the wall 30 of the cannula 110 forms the movable element 122, and the movable element 122 features an orifice 40 therethrough. The movable element 122 is movable between the first position (as schematically illustrated by FIG. 4A) in which the portion of the wall 30 does not contact the valve seat 80, and the second position (as schematically illustrated by FIG. 4B) in which the portion of the wall 30 contacts the valve seat 80 such that the orifice 40 is occluded. Liquid may flow through the orifice 40 to the outlet 115 of the cannula 110 when the movable element 122 is in the first position. However, the liquid is prevented from flowing through the orifice 40 to the outlet 115 when the movable element 122 is in the second position. As such, the valve 120 may prevent both unwanted diffusion of drug from the drug-delivery device 5 into the target organ and unwanted backflow of material from the patient's body into the cannula 110.

In one embodiment, the valve seat 80 is a protrusion (e.g., post) that extends from an inner surface of the cannula 110 towards the movable element 122 (e.g., the flexible portion of the wall 30), as shown schematically in FIGS. 4A and 4B. The protrusion may be substantially identical to the one or more integral mechanical support structures 74 in the lumen 72 of the cannula 110 described above.

In certain embodiments, the movable element 122 moves from the second position (FIG. 4B) to the first position (FIG. 4A) in response to pressure applied to the portion of the wall 30 by fluid within the cannula 110. For example, mechanical (e.g., manual) pressure applied to one or more walls 10, 50 of the reservoir 100 can force fluid through the cannula 110 such that the fluid pressure opens the valve 120. In certain embodiments, the valve 120 opens only when the fluid pressure inside the cannula 110 exceeds a predetermined threshold value greater than the fluid pressure outside the cannula 110. The valve 120 remains closed when the fluid pressure inside the cannula 110 is equal to or less than the fluid pressure outside the cannula 110, thereby preventing biological fluids from flowing backwards into the drug-delivery device 5.

Figure 5A:
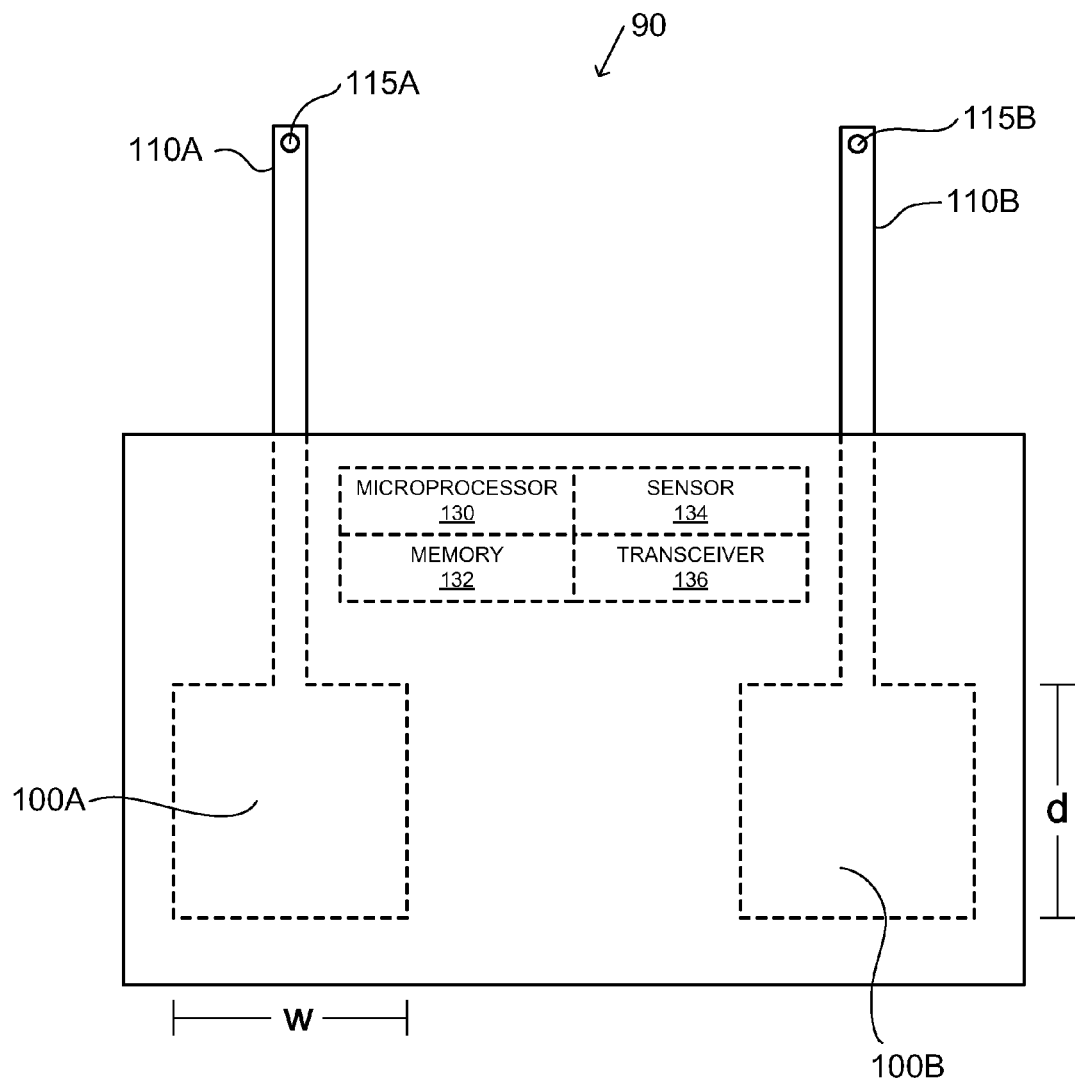
FIG. 5A is a top view of another drug-delivery device in accordance with one embodiment of the invention.

FIG. 5A schematically illustrates a top view of another embodiment of a drug-delivery device 90. As illustrated, rather than featuring a single reservoir 100 having a single cannula 110 in fluid communication therewith, the drug-delivery device 90 includes two reservoirs 100A, 100B. Each reservoir 100A, 100B has a single, different cannula 110A, 110B in fluid communication therewith. In one embodiment, each reservoir 100A, 100B contains a different therapeutic agent in liquid form. This allows for the separate administration of two different drugs, for example in a staged or alternating fashion.

Each reservoir/cannula pair of the drug-delivery device 90 may be a separate pump that features one or all of the elements described above with reference to the embodiments of the drug-delivery device 5 depicted in FIGS. 1A through 4B, and that operates in an analogous fashion. For example, mechanical (e.g., manual) pressure applied to one or more walls of the reservoir 100A can force a first therapeutic fluid through the cannula 110A such that the first fluid exits the outlet 115A. Then, mechanical (e.g., manual) pressure applied to one or more walls of the reservoir 100B can force a second, different therapeutic fluid through the cannula 110B such that the second fluid exits the outlet 115B. Alternatively, each reservoir/cannula pair of the drug-delivery device 90 may in fact be implemented as a separate electrolytic pump, as described below with reference to the embodiments of the drug-delivery device 200 depicted in FIGS. 6 through 10, and be individually controlled in order to deliver to the patient an optimal therapeutic dosage of each of the different drugs.

Figure 5B:
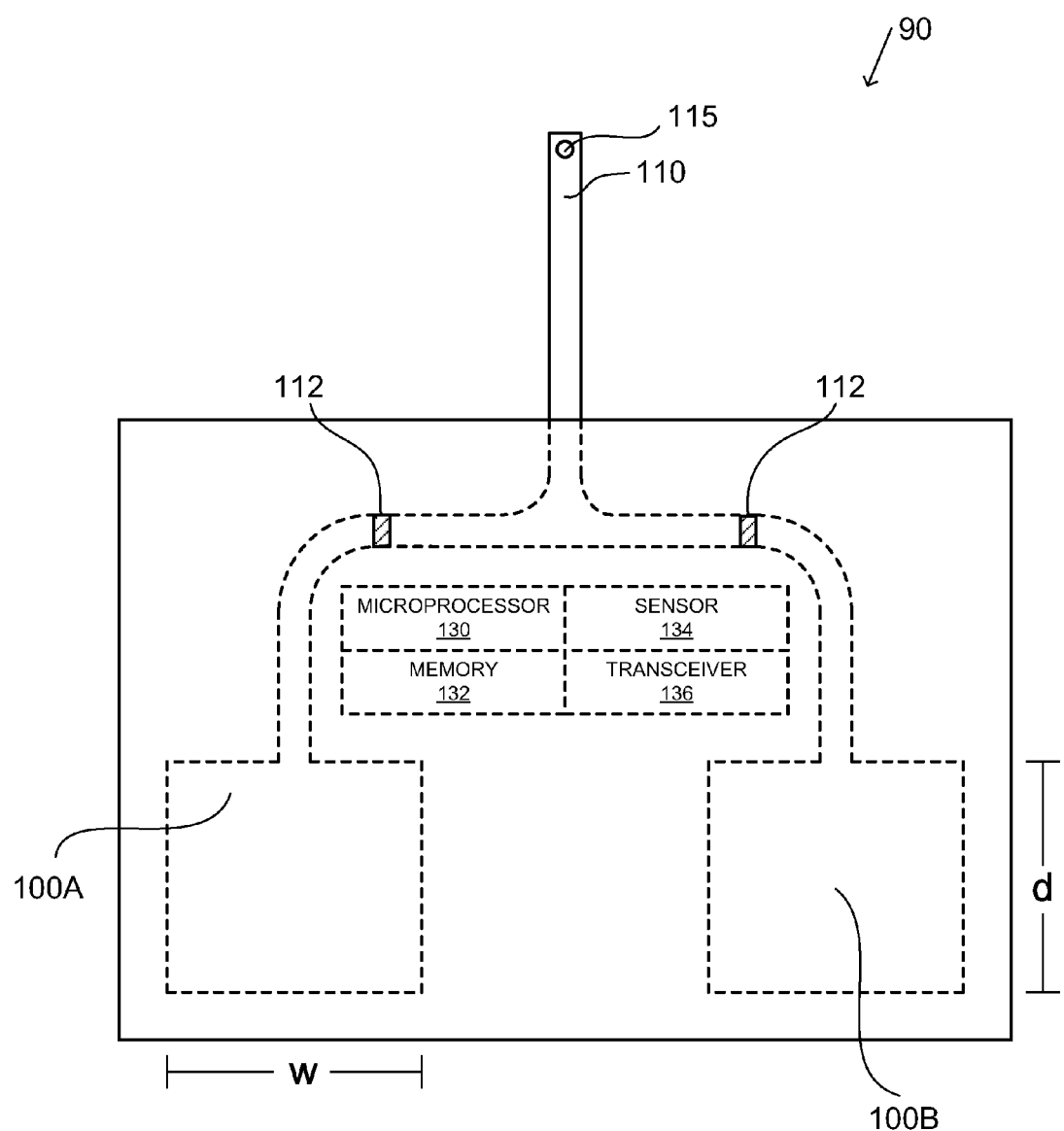
FIG. 5B is a top view of yet another drug-delivery device in accordance with one embodiment of the invention.

While the drug-delivery device 90 is illustrated as having only two reservoir/cannula pairs, it may in fact be manufactured to have three, four, or any number of reservoir/cannula pairs. In addition, rather than having a single, separate cannula in fluid communication with each reservoir (as illustrated in FIG. 5A), a single cannula 110 may in fact be in fluid communication with two, three, four, or more reservoirs, as illustrated in FIG. 5B. In such a case, additional valves 112 may optionally be employed, as illustrated, in the different portions of the cannula 110 that branch off to each reservoir in order to prevent fluidic communication between the reservoirs.

In one embodiment, where the drug-delivery device 90 includes two reservoirs 100A, 100B, the volume of each reservoir ranges from, for example, 63 μL to 105 μL. For example, each reservoir 100A, 100B may have a width w of approximately 3 mm, a depth d of approximately 7 mm, and a height ranging from 3 mm to 5 mm. In such an embodiment, the overall dimensions of the drug-delivery device 90 may be within an 8 mm×8 mm footprint with a height of 3 mm to 5 mm. Processes for manufacturing the drug-delivery device 90 may be as described below with reference to FIGS. 12A-12K and 13A-13M for the single reservoir drug-delivery devices 5 and 200, respectively.

By utilizing two or more reservoirs, different combinations and/or sequences of different drugs may be appropriately employed to treat different maladies. For example, a drug-delivery device 90 featuring two, three, four, or more reservoirs may be employed to deliver appropriate amounts of ranibizumab, pegaptanib, verteporfin, bevacizumab, and/or a steroid, such as fluocinolone or triamcinolone, to treat age-related macular degeneration and/or the macular edema associated with diabetic retinopathy and retinovascular occlusive diseases. In addition, one or more reservoirs in such a device 90 may be employed to deliver, in combination with one or more of those drugs, drugs that prevent beta amyloid deposition in the retina (such as tarenflurbil), anti-human complement blockers to block complement H activation in the eye, and siRNA molecules. In another embodiment, two different isoforms of an anti vascular endothelial growth factor (anti-VEGF) are employed to treat the age-related macular degeneration. In many cases, age-related macular degeneration is caused by polymorphisms on chromosomes 1 and 10. Accordingly, embodiments of the invention may be employed to customize the dosage of different amounts of anti-VEGF variants in order to customize treatment for a patient based on his or her genetic make-up.

As another example, a drug-delivery device 90 featuring three reservoirs may be employed to deliver appropriate amounts of valganciclovir, vitravene, and cidofovir to treat cytomegalovirus retinitis, or a drug-delivery device 90 featuring two reservoirs may be employed to deliver appropriate amounts of two of those drugs to treat the cytomegalovirus retinitis. Similarly, a drug-delivery device 90 featuring two, three, or more reservoirs may be employed to deliver appropriate amounts of any of the drugs identified above for the treatment of glaucoma and/or ocular hypertension, or, alternatively, to deliver appropriate amounts of any of the drugs identified above for the treatment of itching and allergic conjunctivitis, in any combination deemed suitable by a physician. In addition, a drug-delivery device 90 featuring two, three, or more reservoirs may be employed to deliver, in any combination deemed suitable by a physician: i) different drugs for preventing beta amyloid deposition in the brain during the treatment of alzheimers; ii) different steroids for reducing edema following a central nervous system stroke; iii) different steroids for reducing cerebral edema following head trauma; iv) steroids in combination with non-steroidal drugs to suppress inflammatory reactions (e.g., macrophages); v) steroids in combination with anti-cancer drugs (e.g., tumor necrosis factor blocker) to suppress inflammatory reactions (e.g., macrophages); or vi) appropriate amounts of any of the growth factors identified above and/or tumor necrosis growth factor inhibitor for neuroprotection in retinal diseases, glaucoma, and/or brain disorders.

In addition still, two or more different maladies (for example of any of the types described above) may be treated in parallel by a drug-delivery device 90 featuring two, three, or more reservoirs containing different drugs targeted towards treating those different maladies.

In chemotherapy, the delivery of multiple drugs can be very helpful in fighting brain tumors. For example, combinations of bevacizumab (e.g., Avastin®) and CPT-11 can be extremely effective in adult patients suffering from recurrent malignant glioma or in pediatric patients having high risk malignant brain tumors. More specifically, Avastin® and CPT-11 combination therapy has demonstrated rapid clinical and radiographic improvement in patients with relapsed malignant glioma. Some patients have even achieved long term improvement. In addition, MRI scans of recurrent glioma patients treated with Avastin® and CPT-11 (as well as with carboplatin and etoposide) have shown rapid contrast-enhancing tumor shrinkage. In one embodiment, the delivery-device 90 may be employed to pulse boluses of each drug to the brain tumor at different intervals (e.g., Avastin® on odd days and CPT-11 on even days). Since Avastin® and CPT-11 work in different fashions (i.e., Avastin® slows down blood vessel growth by inhibiting vascular endothelial growth factor (VEGF), a protein that plays a major role in angiogenesis and in the maintenance of existing blood vessels throughout the life cycle of a tumor, while CPT-11 disrupts nuclear DNA by inhibiting topoisomerase I, an enzyme that relaxes supercoiled DNA during replication and transcription), pulsing boluses of each drug at different intervals allows the drugs to work without interfering with each other. In addition, steroids may be pulsed intermittently with the Avastin® or CPT-11 to aid the surrounding brain edema during tumor treatment.

As additional examples, specific combinations of the following drugs (e.g., in fluidic form), may be used with the drug-delivery device 90 for the treatment of cancer: i) ranibizumab and CPT-11; ii) letrozole and tamoxifen; iii) doxorubicin and docetaxel; iv) bevacizumab and any chemotherapy drug; v) gemcitabine and CP-870,893 (a CD40 agonist monoclonal antibody); vi) PF-3512676 and a cytotoxic chemotherapy drug; vii) bevacizumab and paclitaxel; viii) docetaxel and sunitinib; ix) bevacizumab and sunitinib; x) lapatinib and letrozole; xi) ixabepilone and capecitabine; and xii) paclitaxel protein-bound and other taxanes.

In one embodiment, in order to control (e.g., stagger or alternate) the delivery of drugs from the multiple reservoirs 100, the drug-delivery device 90 further includes microelectronics, such as a microcontroller or microprocessor 130, memory 132, a sensor 134, and a transceiver 136. More specifically, the memory 132 may store a drug-delivery regimen and the microprocessor 130 may control the delivery of the drugs from the reservoirs 100 to the patient through the one or more cannulas 110 by executing the stored drug-delivery regimen. During execution of the stored drug-delivery regimen, the microprocessor 130 may issue instructions to actuate mechanically, or through electrolysis (as described below), a reservoir/cannula pair (i.e., pump) to release drug therefrom. The stored drug-delivery regimen may be programmed to control, for example, the amount, frequency, and type of drug released based upon any applicable factor or variable. For example, the amount, frequency, and type of drug released may depend upon the time of day (e.g., larger amounts of a particular type of drug may be released more frequently at night when the patient is sleeping), or upon patient-specific factors, such as the severity of the patient's malady, the patient's tolerance for particular types of drugs, the patient's body weight, the patient's genetic make-up (which may be ascertained from, for example, a genetic screening of the patient), etc. In one embodiment, the stored drug-delivery regimen also includes programmable variables identifying the types of drugs contained in the reservoirs 110.

In one embodiment, the sensor 134 gathers feedback from the patient. The microprocessor 130 may then employ the feedback to modify the drug-delivery regimen stored in the memory 132. For example, the sensor 134 may measure the patient's eye pressure and the microprocessor 130 may thereafter increase or decrease the amount and/or frequency at which one or more of the multiple drugs being used in combination is released. As another example, the sensor 134 may determine the residual amount of a first drug that is left in the patient's tissue and then, when residues of the first drug have disappeared, the microprocessor 130 may issue instructions to cause a second drug may be delivered to the patient. In one embodiment, the sensor 134 determines the residual presence of the first drug in the patient's tissue by monitoring the physiological effects of that first drug on the patient. For example, the sensor 134 may measure the patient's reaction to the first drug by sampling and analyzing the patient's blood.

In yet another embodiment, the sensor 134 determines the patient's position (e.g., if the patient's is lying horizontal or standing upright), for example through the use of a device such as a gyroscope. Moreover, the sensor 134 may be employed to monitor the patient's heart rate to determine the patient's activity (e.g., whether the patient is exercising or resting). The microprocessor 130 may then employ such sensed information to deliver a drug, or combinations of drugs, to the patient at an optimal time. For example, upon determining that the patient is lying horizontal and is resting, and that the time of day is 3:00 am, the microprocessor 130 may cause delivery of a drug to the patient that is best administered when one is sleeping. As another example, when the patient's sensed heart rate indicates that he or she is exercising, a drug requiring adequate mixing may delivered to the patient.

The functions described above may be implemented entirely within the drug-delivery device 90 or, alternatively, the microelectronics may also include a transceiver 136 so that, in addition to certain functions being implemented locally, functions may also be implemented remotely. In one embodiment, the transceiver 136 enables wireless communication between the local and remote portions. Moreover, the transceiver 136 may be employed to permit a physician to wirelessly reprogram the drug-delivery regimen.

In general, the microprocessor 130 may be any logic circuitry that responds to and processes instructions fetched from the memory 132. For example, the microprocessor 130 may be one of the many general-purpose microprocessor units manufactured by Intel Corporation of Mountain View, Calif. For its part, the memory 132 may be provided by one or more memory chips capable of storing data and allowing any storage location to be directly accessed by the microprocessor 130. The drug-delivery regimen stored in the memory 132 may programmed using any suitable programming language or languages (e.g., C++, C#, java, Visual Basic, LISP, BASIC, PERL, etc.). The transceiver 136 may be any hardware device, or software module with a hardware interface, that is capable of receiving and transmitting communications, including requests, responses, and commands, such as, for example, inter-processor communications and wireless communications.

The ability to customize therapy by prescribing two or more varying dosages in real-time (e.g., a doctor may wirelessly adjust dosages if needed) also minimizes uncomfortable and dangerous side effects for the patient. One powerful combination for the eye is the ability, using the delivery-device 90, to deliver combination therapy at different times of the day. For example, companies offer timolol and prostaglandin combination therapy (given topically in the same eye drop or in separate eye drops during different times of the day), but those drugs are not typically injected directly in to the eye because of inconvenience and discomfort to the patient. Timolol has a peak action in the eye approximately one hour after the drops are administered, while prostaglandins in the eye has a peak effect approximately four hours after topical administration. Therefore, in accordance with embodiments described herein, the drug-delivery device 90 may stagger drug delivery to match the approved dosing peak effects of combination therapies for diseases such as open-angle glaucoma.

In the prior art, for example, a patient may self administer at 7 pm an FDA approved single eye drop that contains timolol and prostagladins for a peak action of each drug at approximately 8 pm and 11 pm, respectively. In contrast, the drug-delivery device 90 may be programmed to pump each respective drug at different staggered times to reach the same clinically desired effect when applied topically. Because drugs typically have different times of transport across the cornea when administered topically, but are not presented with that challenge when injected directly into the eye using the drug-delivery device 90, the drug-delivery device 90 may be employed to match optimal clinical effects with staggered intracameral injections.

Exemplary fixed combinations of drugs that may be administered to the patient using the drug-delivery device 90 include timolol 0.5%/dorzolamide 2.0%, timolol 0.5%/brimonidine 0.2%, and fixed combinations of prostaglandins plus timolol 0.5%, such as: timolol 0.5%/latanoprost 0.005%, timolol 0.5%/travoprost 0.005%, and timolol 0.5%/bimatoprost 0.03%.

Fixed combinations of drugs injected intracamerally with the drug-delivery device 90 help to avoid medication washout, which may occur when a patient on multiple single drugs instills his or her various medications with too short an interval between eye drops. In fact, with multiple eye drops for multiple drugs, a significant washout effect may occur when one drug causes another drug to be ineffective by increasing outflow before a therapeutic effect has occurred. Moreover, although large clinical trials have shown the fixed combination of timolol/dorzolamide to be equivalent to the unfixed combination (at most time points), real-world studies have demonstrated improved intraocular pressure (IOP) lowering for the fixed combination versus the unfixed combination.

Current limitations with topical combination therapies include the inability to tailor individualized therapy as flexibly as with the component drugs that can be administered using the drug-delivery device 90. The rigidity of topical fixed combination therapy may prevent the optimal dosing frequency or timing of some components (for example, having to use a beta-blocker twice daily when once daily may be sufficient). In various embodiments, the pumps of the drug-delivery device 90 allow for different combination therapies during the day (e.g., drug A and B in morning, drug B in the afternoon, and drug A in the evening). Patients, on the other hand, are not typically able to comply with such complicated dosing schedules. As a result, their doctor may give them one bottle having combination drugs A and B, and ask the patient to take that combination two or three times per day when it may not be necessary, for example, for some dosings of one drug in the evening. In addition, the side effects of drug components may be additive, and drug interactions are often compounded with combinations of therapy. The pumps of the drug-delivery device 90 may, however, achieve the same clinical effect without comprising one drugs efficacy and desired timing.

Figure 6:
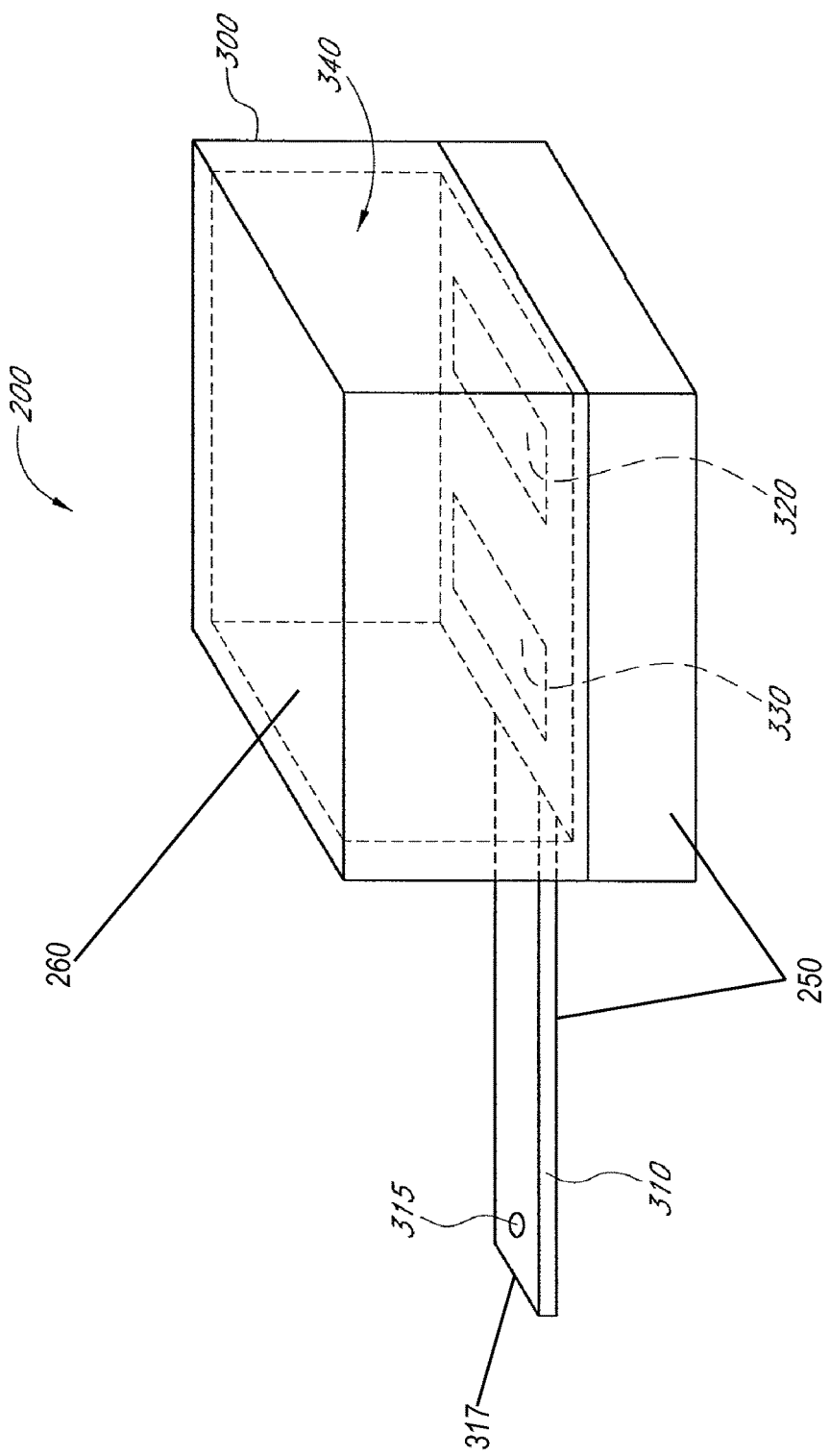
FIG. 6 illustrates a drug-delivery device that utilizes electrolytic pumping in accordance with one embodiment of the invention.

FIG. 6 illustrates yet another embodiment of a drug-delivery device 200. The device 200 includes a reservoir 300, which is configured to contain a liquid comprising a therapeutic agent (e.g., a drug), and a cannula 310 that is in fluid communication with the reservoir 300. The cannula 310 may be manufactured from parylene or other suitable material. At or near its distal end 317, the cannula 310 includes an outlet 315 that is configured to be in fluid communication with a patient (e.g., a patient's eye). The device 200 also includes a first electrode 320, a second electrode 330, and a material 340 that is in electrical communication with the first and second electrodes 320, 330. At least one of the electrodes 320, 330 is planar. To ensure that the material 340 is in electrical communication with both electrodes 320, 330, the electrodes may be interdigitated with one another. In one embodiment, a voltage applied between the first electrode 320 and the second electrode 330 produces gas from the material 340. The produced gas forces the liquid to flow from the reservoir 300, through the cannula 310, to the outlet 315. In other words, the first and second electrodes 320, 330 operate an electrolytic pump that drives liquid from the reservoir 300, through the cannula 310, to the outlet 315.

In greater detail, electrolytic pumps use electrochemically-generated gases to generate pressure that dispenses fluid (e.g., a drug-containing liquid) from one location to another. For example, application of a suitable voltage across two electrodes (typically gold, palladium, or platinum) immersed in an aqueous electrolyte produces oxygen and hydrogen gases that can be used to apply pressure to a piston, membrane, or other transducer. Electrolysis of water occurs rapidly and reversibly in the presence of a catalyst such as platinum, which in the absence of an applied voltage catalyzes recombination of the hydrogen and oxygen to reform water. As described, in certain embodiments, the drug-delivery device 200 uses electrolytically-generated gas to pump the drug from the reservoir 300 through the cannula 310 to the patient. A check valve (not shown) at the distal end 317 of the cannula 310 may be employed to prevent forward flow of drug until enough pressure is generated by the pumping apparatus. Such electrolytic pumping can facilitate the electronic control of drug delivery.

Electrolytic pumps offer several advantages for drug delivery. Their low-temperature, low-voltage, and low-power operation suits them well for long-term operation in vivo. For ocular applications, electrolytic pumps produce negligible heat and can also achieve high stress-strain relationships. Moreover, they lend themselves readily to the use of microelectronics to control the voltage applied to the pump (and therefore the temporal pattern of pressure generation), which allows operation the device 200 in either bolus and/or continuous dosage mode. Radio-frequency (RF) transmission and reception may also be used to provide wireless power and control of the microelectronic circuitry that operates the pump.

Electrolysis in a chamber in fluid communication with its exterior generates gases that force working fluid out of the chamber. Reversing the polarity of the applied voltage can reverse the process, thereby restoring the chamber to its original state. Since a small trickle charge can prevent this reverse process, the drug-delivery device 200 can be held in place with little power (i.e., the device 200 is latchable).

With reference still to FIG. 6, the drug-delivery device 200 may be constructed of a first portion 250 and a second portion 260 mounted thereon. As illustrated, the first portion 250 may include the cannula 310, the first electrode 320, and the second electrode 330. By mounting the second portion 260 onto the first portion 250, the reservoir 300 is formed therebetween. In certain embodiments, the second portion 260 includes a liquid- and gas-impermeable material (e.g., silicone) that is self-sealing to repeated punctures, as described above.

Figure 7A:
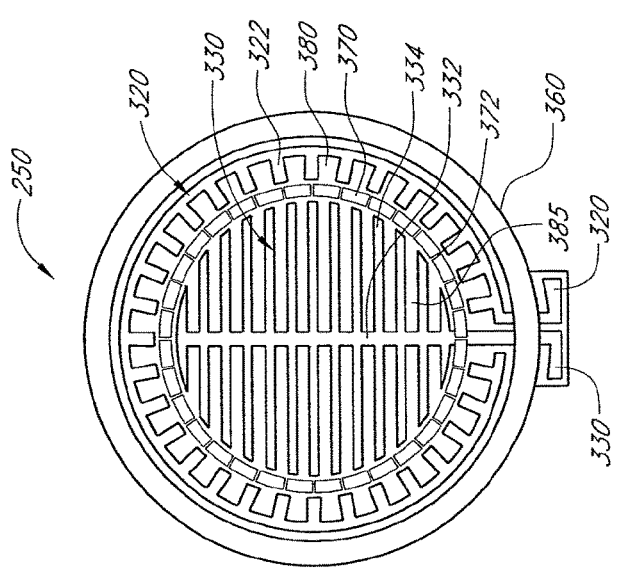
FIGS. 7A and 7B illustrate a top-cross-sectional view and a side-cross-sectional view, respectively, of an electrolysis micropump in accordance with one embodiment of the invention.
Figure 7B:
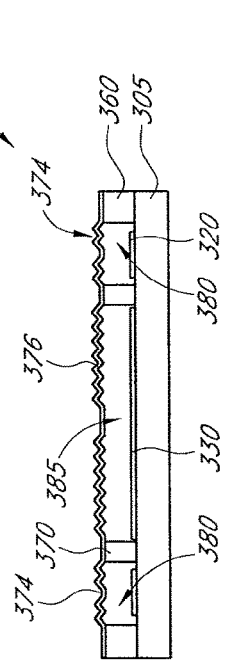

FIGS. 7A and 7B schematically illustrate a top-cross-sectional view and a side-cross-sectional view, respectively, of the first portion 250 of the drug-delivery device 200 in accordance with another embodiment of the invention. As illustrated, the first portion 250 includes a support layer 305, the first electrode 320, and the second electrode 330. The first and second electrodes 320, 330 are positioned over the support layer 305, and at least one of the first electrode 320 and the second electrode 330 is planar.

In certain embodiments, the support layer 305 is liquid- and gas-impermeable and is also electrically insulative such that, absent any conductive material above the support layer 305, the first electrode 320 and the second electrode 330 are electrically insulated from one another. The first electrode 320 and the second electrode 330 are configured to be in electrical communication with a voltage source (not shown) that applies a voltage difference across the first electrode 320 and the second electrode 330.

As illustrated in FIGS. 7A and 7B, in certain embodiments, the first and second electrodes 320, 330 are co-planar with one another. In certain embodiments, at least one of the first and second electrodes 320, 330 is patterned to have elongations or fingers within the plane defined by the electrode. For example, as illustrated in FIG. 7A, the first electrode 320 may be elongate and extend along a generally circular perimeter with radial elongations 322 that extend towards the center of the circular perimeter. For its part, the second electrode 330 may have a center elongate portion 332 with generally perpendicular elongations 334 that extend therefrom. In certain embodiments, the elongations 334 define a generally circular perimeter within the generally circular perimeter of the first electrode 320, as illustrated in FIG. 7A. Other shapes and configurations of the first electrode 320 and the second electrode 330 are also compatible with embodiments of the drug-delivery device 200 described herein.

In certain embodiments, the first portion 250 also includes an outer wall 360 that is liquid- and gas-impermeable. As described more fully below, the outer wall 360 is configured to be bonded to a corresponding wall of the second portion 260 of the device 200.

The first portion 250 of the drug-delivery device 200 may also include a first structure 370 between the first electrode 320 and the second electrode 330. As illustrated in FIGS. 7A and 7B, the first structure 370 may be a generally circular wall extending generally perpendicularly from the support layer 305. In certain embodiments, the first structure 370 includes one or more fluid passageways 372 through which a liquid can flow between a first region 380 above the first electrode 320 and a second region 385 above the second electrode 330, as described more fully below. The first structure 370 may also include a liquid-permeable but gas-impermeable barrier between the first and second regions 380, 385.

In certain embodiments, the first portion 250 also includes a second structure 374 above the first electrode 320 and a third structure 376 above the second electrode 330. The second structure 374 may be mechanically coupled to the first structure 370 and the outer wall 360, as illustrated in FIG. 7B, such that the support layer 305, the outer wall 360, the first structure 370, and the second structure 374 define the first region 380 containing the first electrode 320. In addition, the third structure 376 may be mechanically coupled to the first structure 370, as illustrated in FIG. 7B, such that the support layer 305, the first structure 370, and the third structure 376 define the second region 385 containing the second electrode 330.

The second structure 374 and/or the third structure 376 may be flexible and liquid- and gas-impermeable. For example, the second structure 374 and/or the third structure 376 may include a flexible membrane (e.g., corrugated parylene film). The second structure 374 and/or the third structure 376 may be configured to expand and contract with increases and decreases in pressure in the corresponding first region 380 and/or second region 385. In some such embodiments, both the second and third structures 372, 374 include or represent portions of the same flexible membrane, as illustrated in FIG. 7B.

Figure 8A:
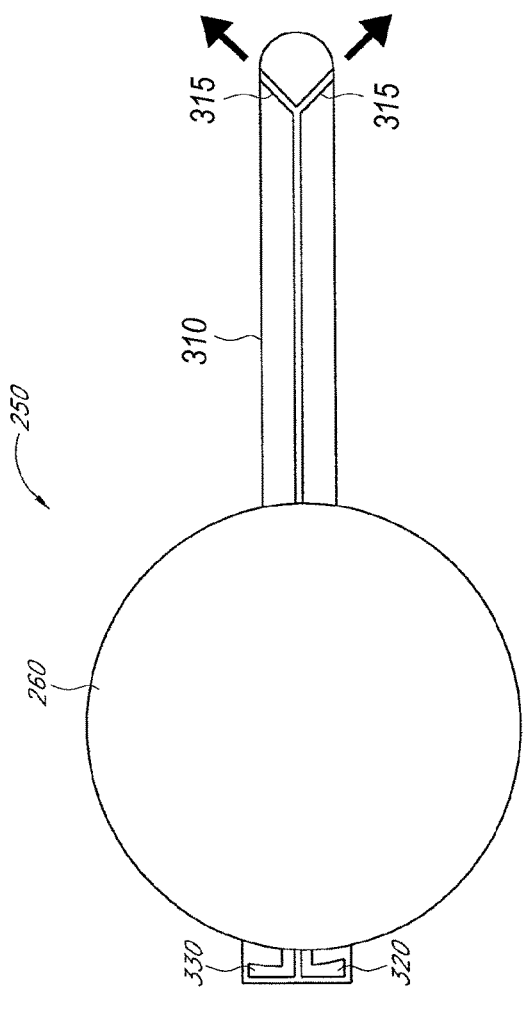
FIGS. 8A and 8B illustrate top and cut-away side views, respectively, of an electrolysis micropump in accordance with one embodiment of the invention.
Figure 8B:
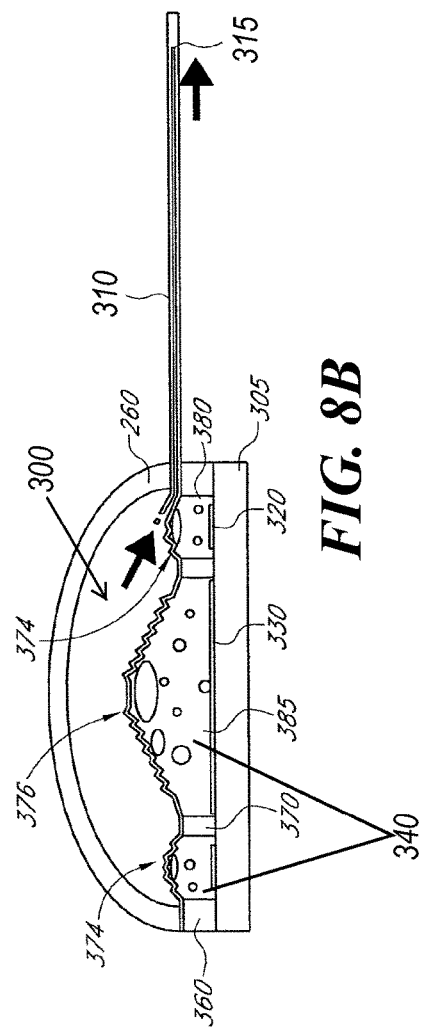

FIGS. 8A and 8B schematically illustrate a top view and a side-cross-sectional view, respectively, of an embodiment of the drug-delivery device 200 including the first and second portions 250, 260. The second portion 260 includes a liquid-impermeable wall that is configured to be bonded to the first portion 250 of the device 200. As illustrated in FIGS. 8A and 8B, the second portion 260 may be bonded to the outer wall 360 of the first portion 250 such that the second portion 260, the second structure 374, and the third structure 376 define the reservoir 300 configured to contain a drug.

In certain embodiments, the first region 380 and the second region 385 contain a material 340 that emits gas when a sufficient voltage is applied to the material 340. For example, in certain embodiments, the material 340 includes water that is electrolytically separated by an applied voltage into hydrogen gas and oxygen gas. As illustrated in FIG. 8B, both the second and third structures 374, 376 may include liquid- and gas-impermeable flexible membranes. Gas generated at the first electrode 320 increases the pressure in the first region 380, thereby flexing the second structure 374 towards the reservoir 300. Furthermore, gas generated at the second electrode 330 increases the pressure in the second region 385, thereby flexing the third structure 376 towards the reservoir 300. The flexing of the second structure 374 and/or the third structure 376 forces liquid (e.g., containing a therapeutic agent, such as a drug) to flow from the reservoir 300, through the cannula 310, to the one or more outlets 315.

In one embodiment, the device 200 restricts gas produced at the first electrode 320 from mixing with gas produced at the second electrode 330. For example, as illustrated in FIG. 8B, when the material 340 comprises water, hydrogen gas produced at the first electrode 320 is generally restricted to the first region 380 and the hydrogen gas produced at the other, second electrode 330 is generally restricted to the second region 385.

Figure 9A:
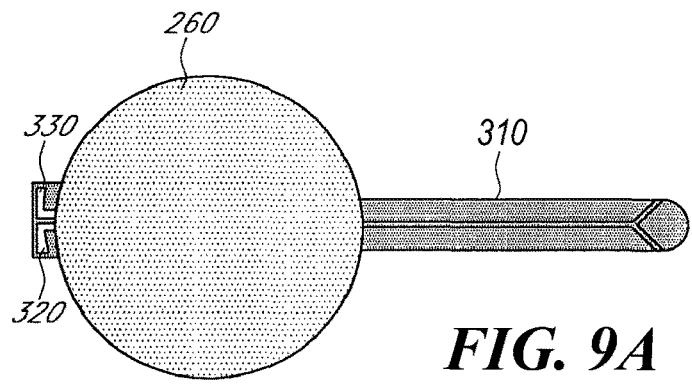
FIGS. 9A-9D illustrate successive cut-away views of a drug reservoir and pump chamber in accordance with one embodiment of the invention.
Figure 9B:
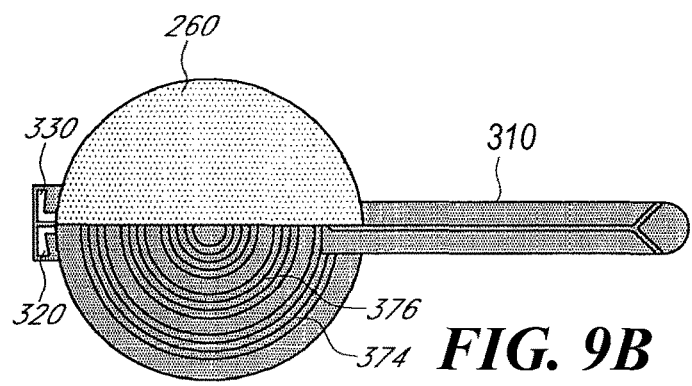
Figure 9C:
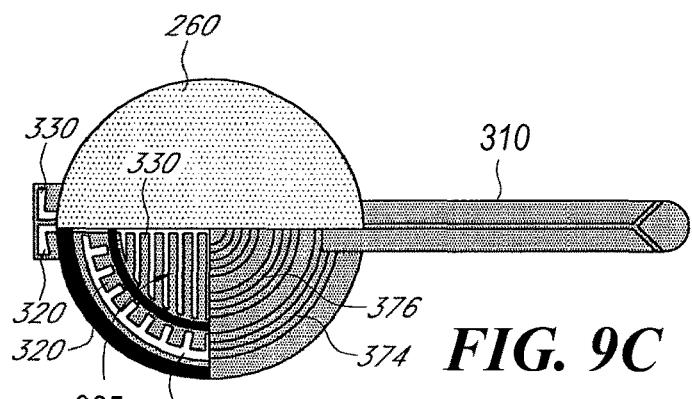
Figure 9D:
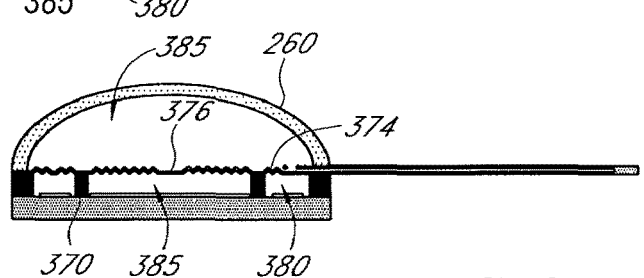

FIGS. 9A-9D schematically illustrate various views of the drug-delivery device 200 of FIGS. 8A and 8B. FIG. 9A schematically illustrates a top view of the device 200 with the first electrode 320, the second electrode 330, the second portion 260, and the cannula 310. FIG. 9B schematically illustrates a top partially cut-away view that shows the first electrode 320, the second electrode 330, the second portion 260, the cannula 310, the second structure 374, and the third structure 376. As shown in FIG. 9B, the second structure 374 and the third structure 376 are portions of a membrane extending across the first portion 250 of the device 200. FIG. 9C shows a portion of the first region 380, the first electrode 320 in the first region 380, the second region 385, the second electrode 330 within the second region 385, the second structure 374, the third structure 376, the second portion 260, and the cannula 310. The device 200 shown in FIG. 9D does not contain either the material 340 or the drug, but otherwise corresponds to the filled device 200 shown in FIG. 8B.

Figure 10:
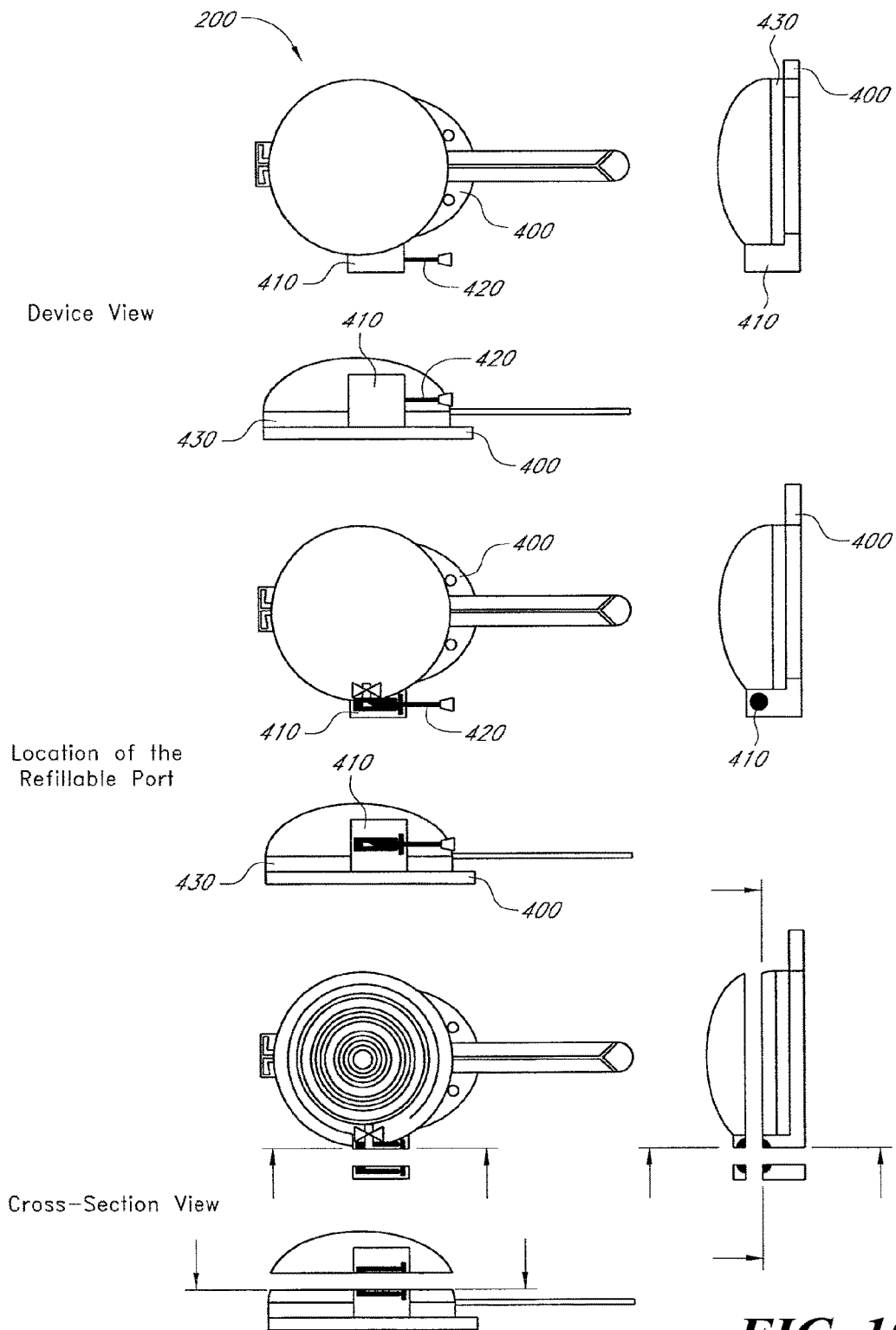
FIG. 10 illustrates one embodiment of a drug-delivery system with drug reservoir, cannula, valving, pump, refillable port, and suture tabs.

FIG. 10 schematically illustrates various views of the drug-delivery device 200 that includes an injection port 410 configured to receive an injection needle 420. In one embodiment, the injection port 410 is part of the first portion 250 of the device 200, while in another embodiment the injection port 410 is part of the second portion 260 of the device 200. The injection port 410 is in fluid communication with the reservoir 300 of the device 200 to facilitate refilling of the device 200 while the device 200 is implanted. In addition, as illustrated in FIG. 10, the device 200 may include suture tabs 400 for fastening the device 200 to a patient's body (e.g., to the surface of the patient's eye).

Figure 11:
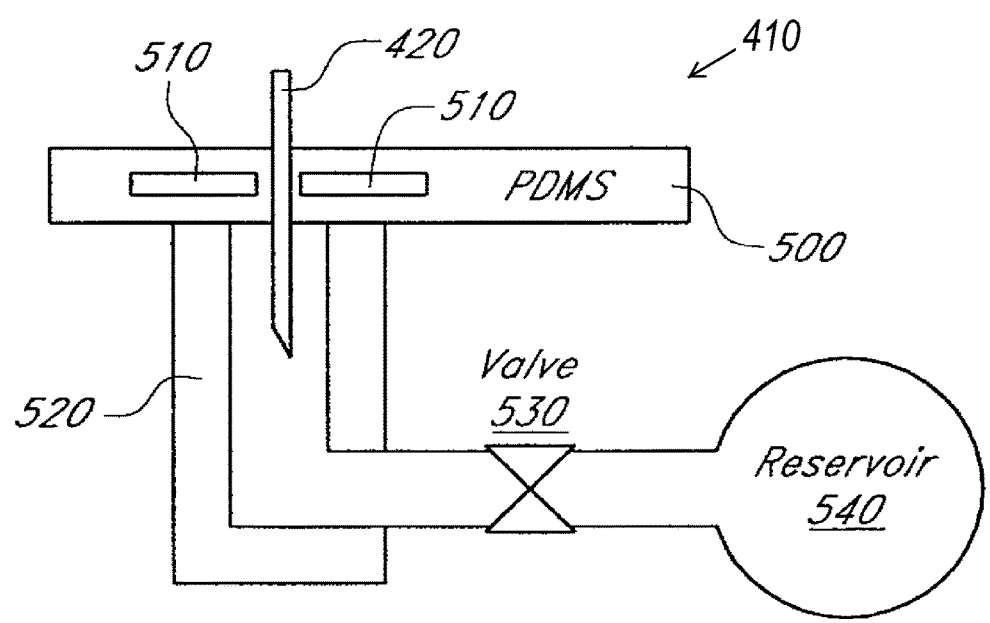
FIG. 11 illustrates the internal structure of one type of injection port on the reservoir in accordance with one embodiment of the invention.

FIG. 11 schematically illustrates the internal structure of an exemplary injection port 410. Injection needle 420 pierces a surface 500 of the injection port 410 through needle injection guide 510, and thereby gains access to injection vestibule 520. Injection of fluid from the needle 420 into the vestibule 520 forces liquid through the injection port valve 530 and into the reservoir 540.

In certain embodiments, the device 200 is powered by an internal battery (not shown), while in other embodiments, the device 200 is powered by an external source (not shown). Alternatively, both a battery and an external source may be used. For example, even though the power can be recharged wirelessly, a smaller battery may be used to store the power for a week, thereby advantageously keeping the device small and minimally invasive.

The external source can be electrically coupled to the device 200 using wires or by wireless means (e.g., by using RF transmitters and receivers). By utilizing an external source and avoiding the use of an internal battery, the device 200 can advantageously be made even smaller, and therefore less invasive. In addition, by wirelessly controlling the operation of the device 200 (e.g., turning it on and off), a handheld transmitter can be programmed to send a signal that communicates with the device to power the device when needed. For example, at times when less drug is needed, less power is transmitted, and less drug is pumped. There may also be some threshold cutoff on the external power applicator that limits the implant from pumping too much drug. Wireless power may be inductively imparted through the use of coils built into the implant and the external transmitter.

In another embodiment, the device 200 includes an integrated circuit for controlling operation of the device 200. Examples of integrated circuits compatible with embodiments of the drug-delivery devices described herein include, but are not limited to, single-chip application specific integrated circuits (ASICs) and application specific standard products (ASSPs) that have become more common for implantable medical applications. In some embodiments, such integrated circuits consume as little power as possible to, for example, extend battery life and therefore lengthen the time between invasive replacement procedures. In addition, the device 200 may include microelectronics to control the dosage and release, sensors for feedback control, anchoring structures to hold the device in place, supports to keep the reservoir from collapsing on itself when emptied, filtering structures, additional valves for more accurate flow control, a flow regulator to remove the adverse effects of pressure on drug delivery, and a programmable telemetry interface.

Figure 12:
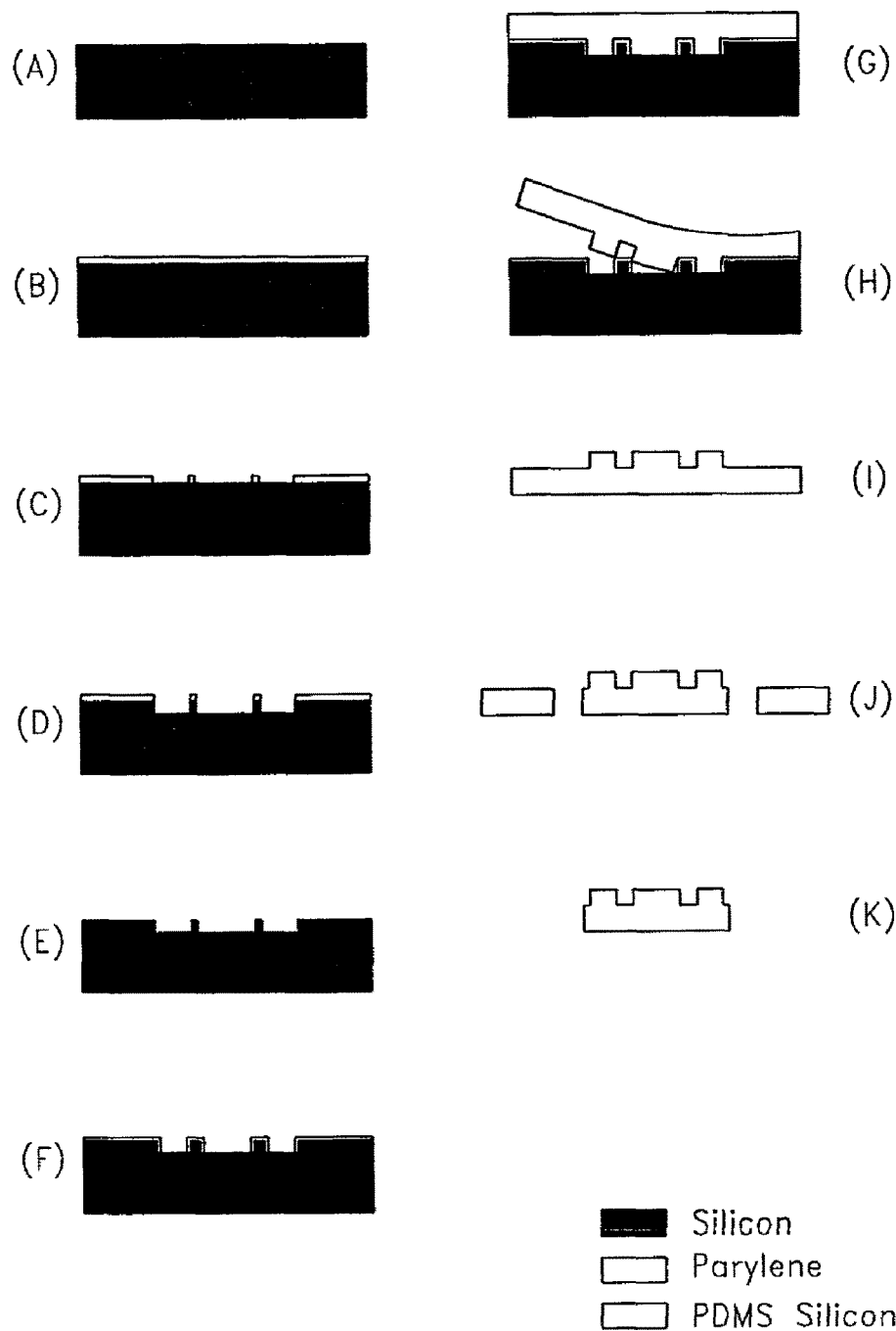
FIGS. 12A-12K illustrate a process flow for fabricating a silicon mask and making a molded polydimethylsiloxane (PDMS) layer in accordance with one embodiment of the invention.

In one embodiment, as illustrated in FIGS. 1A and 1B, the drug-delivery device 5 includes three individual structural layers 10, 20, 50. One, two, or all three of the layers 10, 20, 50 may be made of a biocompatible polymer, such as PDMS or parylene. In one embodiment, at least one of the structural layers 10, 20, 50 is formed using a lithographic process (e.g., soft lithography). FIGS. 12A-12K schematically illustrate an exemplary lithographic process. As illustrated in FIG. 12A, a substrate (e.g., a silicon wafer) is provided. A photoresist layer may then be formed on the substrate (e.g., by spin-coating a light-sensitive liquid onto the substrate), as shown in FIG. 12B. Suitable photoresists are well-known to those skilled in the art and include, but are not limited to, diazonaphthoquinone, phenol formaldehyde resin, and various epoxy-based polymers, such as the polymer known as SU-8. As illustrated in FIG. 12C, the photoresist layer may then be patterned to cover a first portion of the substrate and to not cover a second portion of the substrate. For example, ultraviolet light may be shone through a mask onto the photoresist-coated wafer, thereby transferring the mask pattern to the photoresist layer. Treatment of the wafer by well-known photoresist development techniques can then be used to remove the portions of the photoresist layer that were exposed to the ultraviolet light. Persons skilled in the art of lithographic techniques are able to select appropriate materials and process steps for forming the patterned photoresist layer in accordance with the embodiments described herein.

As illustrated in FIG. 12D, the portion of the substrate that is not covered by the patterned photoresist layer may be etched (e.g., by deep reactive-ion etching), thereby leaving untouched the portions of the silicon wafer protected by the photoresist layer. As illustrated in FIG. 12E, the patterned photoresist layer may then be removed. For example, after washing with a solvent, such as acetone, the photoresist layer is removed and the entire wafer can be cleaned through use of oxygen plasma to remove any remaining photoresist. As illustrated in FIG. 12F, a mold release layer (e.g., parylene, a widely-used polymer of p-xylene) may be formed on the substrate to facilitate removal of the PDMS layer from the silicon wafer. Other materials can be used as the mold release layer in other embodiments. As illustrated in FIG. 12G, a structural layer (e.g., PDMS silicone) may be formed on the mold release layer. For example, PDMS can be poured over the silicon wafer and allowed to cure either by standing at room temperature or accelerated by heating (e.g., to 75° C. for 45 minutes). As illustrated in FIG. 12H, the structural layer may then be removed from the substrate, thereby providing the structural layer illustrated in FIG. 12I. In certain embodiments, the molded PDMS layer contains multiple copies of the structural layer, and each copy of the structural layer is separated from the others. Excess material can be removed from the structural layer, as illustrated in FIG. 12J, thereby providing the structural layer illustrated in FIG. 12K, which is ready for assembly with the other structural layers.

The individual structural layers can be assembled and bonded together in certain embodiments by treating the surface of one or more of the structural layers with oxygen plasma for about one minute, although the time is not critical. Oxygen plasma changes the surface of the PDMS from hydrophobic to hydrophilic.

In certain embodiments, with reference again to FIG. 1A, the bottom layer 50 and the middle layer 20 are placed into a plasma chamber with the sides that are to be bonded facing the plasma. Once the surfaces have been treated, the two pieces 20, 50 may be aligned with the aid of a polar liquid (e.g., ethanol, water, etc.). The liquid preserves the reactive hydrophilic surface providing more time to align the two layers. It also makes the two pieces 20, 50 easier to manipulate for alignment since it lubricates the surfaces, which are otherwise sticky. The two-layer assembly can then be placed back into the chamber along with the top layer 10 and the treatment and alignment procedure repeated. The entire assembly can then be baked (e.g., at 100° C. for 45 minutes) to reinforce the bonds. In practice, the bonded silicone appeared homogeneous by scanning electron microscopy and optical observation. Tests with pressurized $N_2$ showed that the bonded silicone assembly withstood pressures of at least 25 psi.

With reference to FIGS. 1A and 1B, in certain embodiments, the orifice 40 is made by inserting a small diameter coring needle into a sheet of silicone rubber that later forms the upper surface of the cannula 110. Other methods can also be used to generate this feature. The coring needle removes material to create the orifice 40. The valve seat 80 may be a post that protrudes from the bottom of the cannula 110 and extends the height of the channel 72 to meet the top of the cannula 110. During assembly, the orifice 40 is centered over the valve seat 80 and rests on it to form the valve 120. In this configuration, the valve 120 is said to be "normally-closed" and fluid will not pass through. Fluid pressure in the cannula 110 exceeding a certain value (i.e., a cracking pressure) opens the valve 120 and allows fluid to exit the drug-delivery device 5 through a gap between valve seat 80 and the movable element 122, as illustrated in FIG. 4A.

FIGS. 13A-13M schematically illustrate one exemplary process for forming a drug-delivery device that includes electrolytic pumping, such as the drug-delivery device 200 depicted in FIG. 6, although other processes may also be employed in forming the drug-delivery device.

Figure 13:
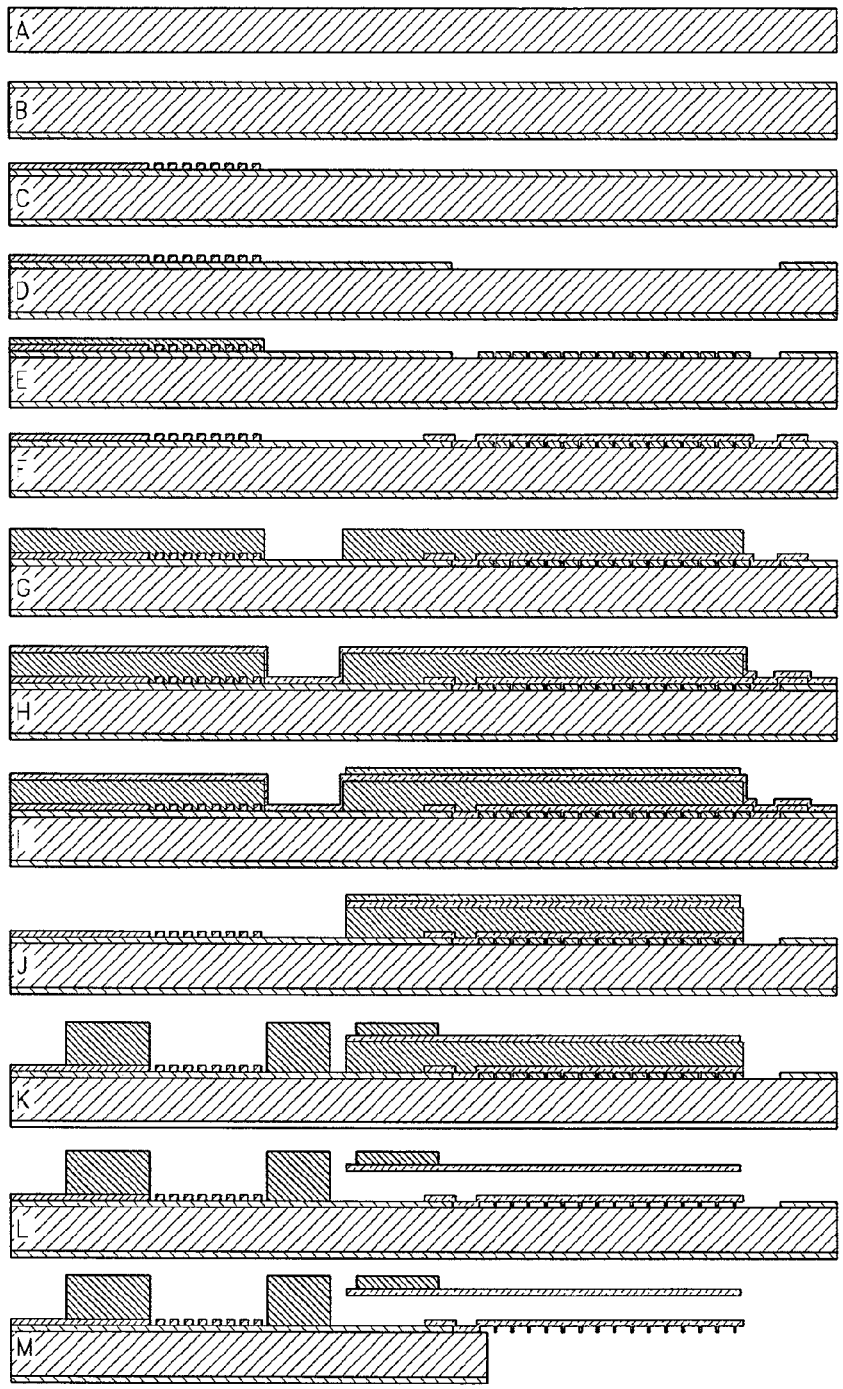
FIGS. 13A-13M illustrate a process flow for fabricating the base layer of an implantable drug-delivery device that includes electrodes for electrolytic pumping and an integral cannula in accordance with one embodiment of the invention.

As illustrated in FIG. 13A, a bare silicon substrate may be provided and, as illustrated in FIG. 13B, a dielectric layer (e.g., a thermal silicon dioxide layer about 4000 Å thick) may be grown on the silicon substrate. This silicon oxide layer electrically insulates the substrate and electrolysis electrodes.

As illustrated in FIG. 13C, electrolysis electrodes (e.g., made of Ti/Pt, 200 Å and 2000 Å thick, respectively) may be then formed over the dielectric layer (e.g., deposited and lithographically patterned). The dielectric layer may be patterned and etched briefly with $XeF_2$ to remove a portion of the dielectric layer, thereby exposing a portion of the substrate. This process can also roughen the exposed silicon surface, as illustrated in FIG. 13D. A first sacrificial photoresist layer (e.g., 5 µm thick) can be spun and patterned on the substrate, as illustrated in FIG. 13E. The first sacrificial photoresist layer facilitates the release of the cannula from the supporting silicon substrate at the end of the fabrication process. A first structural layer (e.g., a 7.5 µm thick parylene layer) can then be deposited and patterned on the first sacrificial layer, as illustrated in FIG. 13F. The first structural layer will become the bottom wall of the drug-delivery cannula. As illustrated in FIG. 13G, a second sacrificial layer (e.g., a 25 µm thick photoresist layer, spun and patterned) can be formed over the first structural layer. As illustrated in FIG. 13H, a second structural layer (e.g., a 7.5 µm thick parylene layer) can then be deposited on the second sacrificial layer. The second structural layer will become the top and side walls of the cannula. The first and second structural layers can then be patterned, as illustrated in FIGS. 13I and 13J. For example, a Cr/Au etch mask layer for removing unwanted parylene (200 Å and 2000 Å thick, respectively) can be deposited and patterned on the substrate, as illustrated in FIG. 13I. The parylene can be patterned in an oxygen plasma through use of the Cr/Au masking layer, as schematically illustrated in FIG. 13J. A third structural layer (e.g., an SU-8 photoresist layer 70 μm thick) can be spun and patterned on the substrate, as illustrated in FIG. 13K. The SU-8 layer can support the cannula and prevent its collapse when a drug reservoir is attached to the base layer. The sacrificial photoresist layers are then removed by dissolving them in acetone, as illustrated in FIG. 13L. The cannula can then be peeled up from the surface of the roughened silicon substrate and broken off the silicon substrate directly beneath the cannula to form a free-standing cannula, as illustrated in FIG. 13M.

In one embodiment, the drug-delivery device 5, 90, 200 is implanted by attaching the main body of the device 5, 90, 200 to the top of a patient's eye and inserting the cannula 110, 310 into the anterior or the posterior segment of the eye. The device 5, 90, 200 may be affixed to the eye through use of current ophthalmic techniques such as sutures or eye tacks. In one embodiment, a method of using the device 200 includes applying a first voltage between the first and second electrodes 320, 330 to produce gas from the material 340 in electrical communication with the electrodes. The gas forces liquid to flow from the reservoir 300, through the cannula 310, to the outlet 315 of the device 200. In certain embodiments, the method also includes applying a second voltage between the first electrode 320 and the second electrode 330 to produce the material 340 from the gas. In this way, the device 200 is used in a reversible manner in which the material 340 is regenerated from the gases, thereby avoiding having to refill the device 200 with the material 340. In certain embodiments, the material 340 comprises water and the gas comprises hydrogen gas and oxygen gas. In certain embodiments, the first voltage and the second voltage are opposite in sign.

EXAMPLE

A device having a flexible parylene transscleral cannula allowing for targeted delivery to tissues in both the anterior and posterior segments of a patient's eye is described below. This electrochemically driven drug-delivery device was demonstrated to provide flow rates suitable for ocular drug therapy (i.e., pL/min to μL/min). Both continuous and bolus drug-delivery modes were performed to achieve accurate delivery of a target volume of 250 nL. An encapsulation packaging technique was developed for acute surgical studies and preliminary ex vivo drug-delivery experiments in porcine eyes were performed.

The electrolysis of water results in the phase transformation of liquid to gas and provides the actuation used to drive drug delivery in this example device. The net result of the electrolysis is the production of oxygen and hydrogen gas that contributes to a volume expansion of about a thousand times greater than that of the water used in the reaction. This gas evolution process proceeds even in a pressurized environment (e.g., 200 MPa).

To drive gas generation and thus pumping, current control is useful due to its direct correlation to pump rate and volume. If current is used to drive the reaction, the theoretical pump rate ($q_{theoretical}$ in m$^3$/s) at atmospheric pressure is given by:

$$q_{theoretical} = 0.75(I/F)V_m,$$

where I is current in amperes, F is Faraday's constant, and $V_m$ is the molar gas volume at 25° C. and atmospheric pressure. The theoretical generated or dosed gas volume ($V_{theoretical}$ in m$^3$) can be determined by:

$$V_{theoretical} = q_{theoretical} t,$$

where t is the duration (in sec) that the current is applied. The efficiency (η) of an electrolysis actuator as a pump can be defined as:

$$\eta = V_{experimental}/V_{theoretical},$$

where $V_{experimental}$ is the actual volume of the generated hydrogen and oxygen gases. Efficiency in electrochemical systems is affected by a number of parameters including electrode parameters (e.g., material, surface area, geometry, and surface conditions), mass transfer parameters (e.g., transport mode, surface concentration, and adsorption), external parameters (e.g., temperature, pressure, and time), solution parameters (e.g., bulk concentration of electroactive species, concentration of other species and solvent), and electrical parameters (e.g., potential, current, and quantity of electricity).

The electrolysis pump included two interdigitated platinum electrodes immersed in an electrolyte. This electrode geometry improves pumping efficiency by reducing the current path through the solution, which serves to lower the heat generation. The gasses generated resulted in an internal pressure increase in the sealed reservoir, which caused drug to be delivered through the cannula and into the patient's eye. Electrolysis is a reversible process and ceases when the applied signal is turned off, thereby allowing the gradual recombination of hydrogen and oxygen to water.

Pumped drug entered the flexible transscleral cannula through a small port connected to the pump, while the generated gases remained trapped inside the reservoir. Parylene was selected as the cannula material for its mechanical strength, biocompatibility, and ease of integration. It is a USP Class VI material suitable for the construction of implants and is well-established as a MEMS material. The pump/cannula portion was fabricated using silicon micromachining and the reservoir portion by the casting of silicone rubber against a master mold.

More specifically, the fabrication process of the pump and cannula chip started with a thermally oxidized silicon substrate (5000 Å). LOR 3B (MicroChem Corporation, Newton, Mass.) was spun on at 3 krpm followed by AZ 1518 (AZ Electronic Materials, Branchburg, N.J.) at 3 krpm. Ti—Pt (200/2000 Å) was e-beam evaporated and patterned by lift-off in a ST-22 photoresist stripper (ATMI, Danbury, Conn.) to define the interdigitated electrodes. A second lithography step was performed (AZ 1518 at 3 krpm) to define the cannula footprint. The oxide layer was etched using buffered HF acid to expose the Si below. The photoresist was stripped and then the exposed Si was roughened by two cycles of XeF$_2$ etching. The first sacrificial photoresist layer (AZ 4620 spun at 2.75 krpm and hard baked to yield a 5 micron thick layer) was applied to facilitate release of the cannula from the substrate. The first parylene C layer (7.5 microns) forming the bottom of the cannula was deposited followed by thermal evaporation of a 2000 Å thick Cr etch mask. Following lithography (AZ 4620 at 500 rpm), the Cr was etched in Cr-7 (Cyanteck, Fremont, Calif.) and the photoresist stripped. The parylene layer was then patterned in an oxygen plasma and the Cr etch mask was removed using Cr-7. A second photoresist sacrificial layer was deposited (AZ 4620 spun at 450 rpm and hard baked to yield a 25 micron thick layer) to define the channel height. A second parylene layer of 7.5 microns was deposited to complete the cannula. To define the cannula from the parylene/photoresist/parylene sandwich, Ti/Au (200/2000 Å) was deposited as an etch mask. The etch mask was patterned (AZ 4620 spun at 425 rpm) and etched first with Au etchant TFA (Transene Company, Inc., Danvers, Mass.) and then 10% HF. Finally, the sandwich was etched in oxygen plasma and the masking layer was stripped (Au etching TFA and 10% HF). Following the etch, the entire wafer was cleaned in 5% HF dip and by exposure to oxygen plasma. SU-8 2200 (MicroChem Corporation, Newton, Mass.) was spun at 2200 rpm resulting in a 70 micron thick layer after post baking. The sacrificial photoresist was removed by dissolving in a 40° C. acetone solution for one day. The individual cannulae were released manually by gently lifting them off the substrate. Finally, individual dies were separated and the remaining silicon beneath each cannula was removed by scribing and breaking it off.

The pump chip containing the electrolysis actuator and cannula was combined with the drug reservoir and electrical wiring. Electrical wires were bonded to the electrode contact pads using OHMEX-AG conductive epoxy (Transene Company, Inc., Danvers, Mass.). The epoxy was cured at 150° C. for 15 hours under vacuum. The pump chip and reservoir were then assembled using an encapsulation technique based on silicone soft lithography as described above.

To shape the package to fit comfortably on the curved contour of the eyeball, a silicone spacer (SYLGARD 184, Dow Corning, Midland, Mich.) was casted against a stainless steel sphere of 17.5 mm in diameter. This layer of partially cured silicone (10:1 base to curing agent ratio) was cured at 65° C. for 20 minutes. The sphere was removed and the resulting crater was filled with wax. A silicone reservoir was prepared by casting against a conventionally machined acrylic mold, partially cured at 65° C. for 20 minutes. The mold produced a reservoir with internal dimensions of 6 mm×6 mm×1.5 mm. The silicone reservoir was aligned to the chip and spacer and the parylene cannula was then immersed in DI water, which serves as a mask to prevent coating by silicone rubber during the encapsulation step, thereby exploiting the hydrophobicity of silicone rubber. The stack was immersed in silicone prepolymer and cured at room temperature for 24 hours. Extraneous silicone material was removed from the device to complete the assembly process.

To investigate the performance of the electrolysis pump, experiments examining continuous delivery, bolus delivery, pump efficiency, gas recombination, and backpressure were conducted. For these tests, a custom testing apparatus was laser-machined (Mini/Helix 8000, Epilog, Golden, Colo.) in acrylic. The experimental setup included a computer-controlled CCD camera (PL-A662, PixeLINK, Ottawa, Ontario, Canada) for collecting flow data from a calibrated micro-pipette (Accu-Fill 90, Becton, Dickinson and Company) attached to the output port of the test fixture. Testing was performed using deionized water as the electrolyte. The electrolysis was initiated under constant current conditions (50 µA to 1.25 mA) for continuous delivery operation. The relationship between efficiency and recombination of hydrogen and oxygen to water was studied.

Bolus delivery was also examined A constant current pulse (0.5, 1.0, and 1.5 mA) was applied for 1, 2, and 3 seconds. Repeated trials were performed (n=4) to obtain average dosing volume. Normal IOP ranges from 5-22 mmHg (15.5±2.6 mmHg (mean±SD)). Values outside this range correspond to abnormal IOP, which is a characteristic of glaucoma (>22 mmHg). Thus, it is helpful to characterize pump performance under these physiologically relevant conditions. The experimental setup was modified to include a water column attached to the outlet of the micro-pipette. Backpressure was applied to the drug-delivery device by adjusting the height of the water column. Data was collected for backpressures corresponding to normal IOP (20 mmHg) and abnormal IOP (0 and 70 mmHg).

The prototype drug-delivery devices were implanted in enucleated porcine eyes. Preliminary ex vivo surgical modeling in enucleated porcine eyes is useful to prepare for device demonstration in vivo. The operation of each surgical device was tested prior to the surgical experiment to check for clogs and integrity of the electrical connections. The drug reservoir was filled with dyed deionized water and then the reservoirs were manually depressed, which generates sufficient pressure to expel the fluid from the reservoir. A second test was conducted to verify operation of the electrolysis pump by connecting to an external power supply and driving fluid from the reservoir by electrolysis pumping. An enucleated porcine eye was prepared for the surgical study and a limbal incision was made (between the cornea and sclera). The cannula was implanted through the incision into the anterior chamber. The enucleated porcine eye was pressurized at 15 mmHg by using an infusion line. Constant current (0.5 mA) was applied for 1 minute. The device was surgically removed after the experiment.

Figure 14:
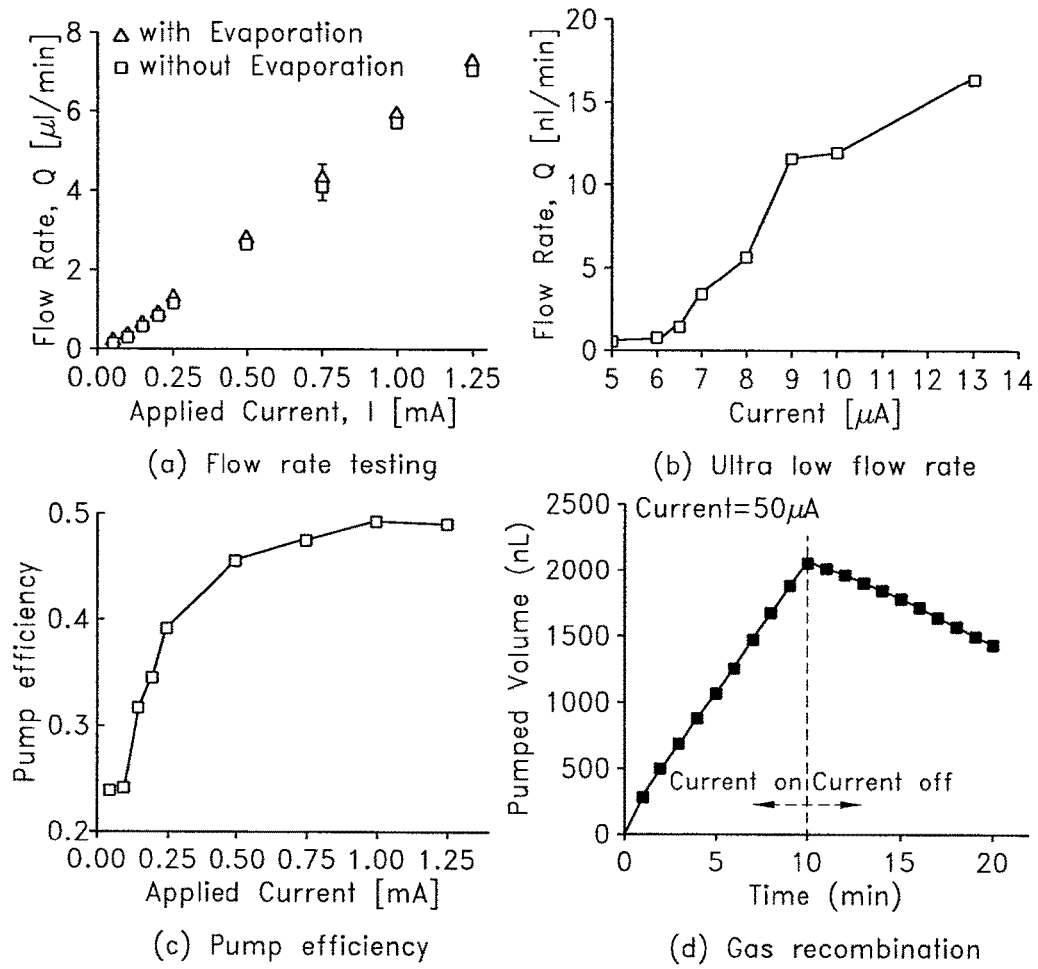
FIG. 14 illustrates (a) flow-rate testing results for an exemplary electrolysis pump; (b) ultra-low flow rate testing results for the exemplary electrolysis pump; (c) the pump efficiency as calculated from the flow delivery data; and (d) the typical gas recombination observed in the pump.

The electrolysis pump was operated at flow rates in the pL/min to µL/min range using driving currents from 5 µA to 1.25 mA (FIGS. 14A and 14B). The highest rate was 7 µL/min for 1.25 mA and the lowest was 438 pL/min at 5 µA. Both data sets are corrected to compensate for the evaporation of fluid during testing. Flow rates below about 2 µL/min are preferred for ocular drug delivery. This is consistent with naturally occurring flow rates in the eye; the ciliary body of the eye produces aqueous humor at 2.4±0.6 µL/min in adults. As current decreases, it was observed that pumping efficiency, which ranged from 24-49%, also decreased (FIG. 14C). Electrolysis-driven pumping efficiency is affected by the competitive recombination of hydrogen and oxygen gases to water. This effect is further enhanced by exposure to the platinum electrolysis electrodes that serve to catalyze the recombination reaction. In FIG. 14D, a typical accumulated volume curve is shown that illustrates the effect of recombination after the applied current is turned off. The measured recombination rate was 62 nL/min.

Figure 15:
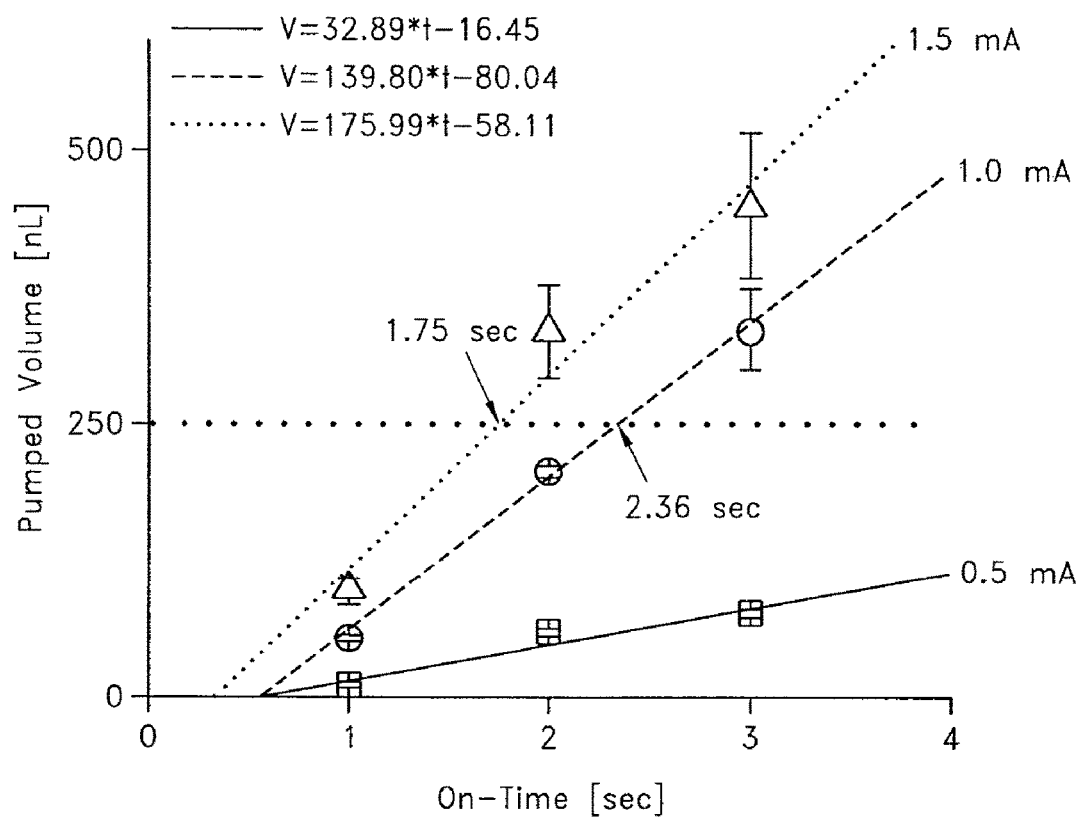
FIG. 15 illustrates bolus delivery of 250 nL doses using current pulses in an exemplary electrolysis pump.
Figure 16:
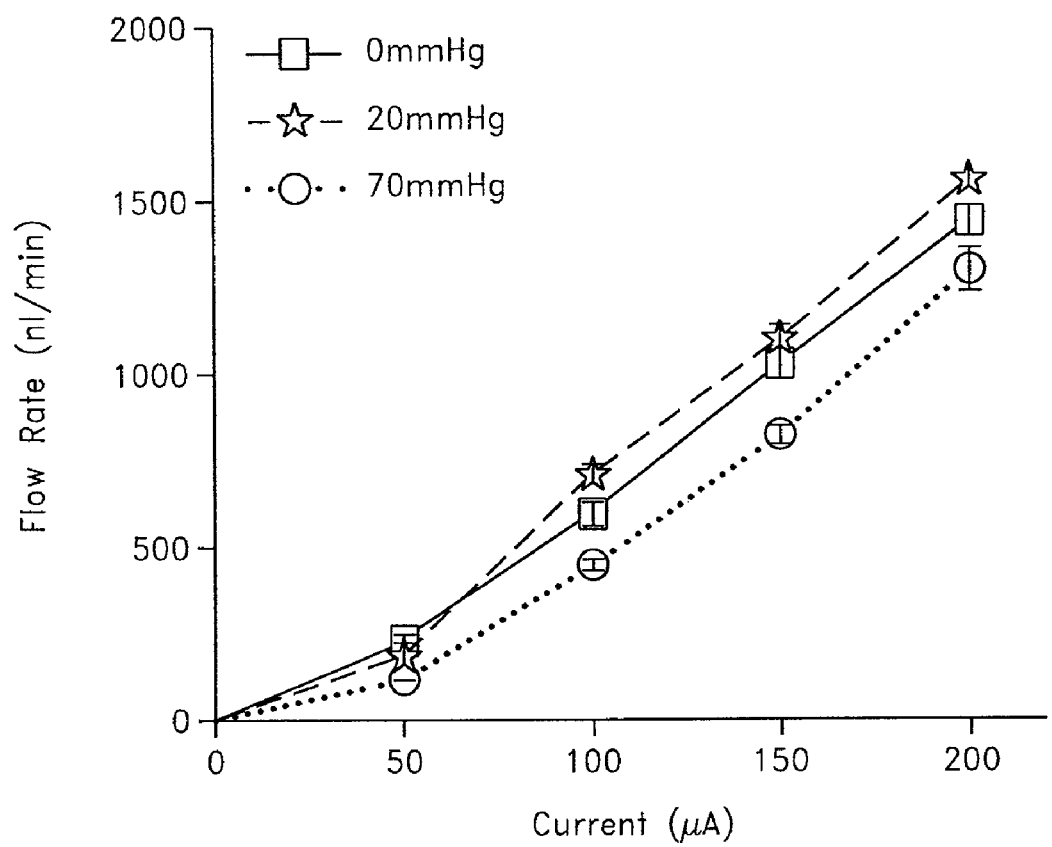
FIG. 16 illustrates the flow performance of an exemplary electrolysis pump under typical physiological back pressures.

Bolus delivery mode was also evaluated (FIG. 15). If the desired dosing regimen is 250 nL per dose, this volume can be obtained by driving the pump for a short duration that is determined by the magnitude of the applied current. For example, a 1.0 mA driving current will dose 250 nL in 2.36 seconds. For 1.5 mA current, the pulse time can be set as 1.75 seconds. Under normal operation in the eye, the drug-delivery device will experience a backpressure equivalent to the IOP of the eye. Benchtop experiments indicated that the pump was able to supply sufficient drug flow over the range of normal and abnormal IOP equivalent backpressures (FIG. 16). The flow rates varied 30% compared to normal IOP over the tested backpressure range.

Initial surgical results showed promising results in enucleated porcine eyes. Following removal of the device after the surgical experiment, post surgical examination of the cornea revealed a small blue spot above the iris near the position of the cannula tip indicating that dye was delivered into the eye.

Additional details on some of the drug-delivery devices described herein may be found in U.S. patent application Ser. No. 11/686,310 entitled "MEMS Device and Method for Delivery of Therapeutic Agents," the disclosure of which is hereby incorporated herein by reference in its entirety.

Having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A drug-delivery device, comprising:
   a first reservoir for containing a first liquid that comprises or consists essentially of a first therapeutic agent;
   a second reservoir for containing a second liquid that comprises or consists essentially of a second therapeutic agent different from the first therapeutic agent; and
   a cannula having first, second and third portions, the second and third portions branching off from the first portion to communicate fluidically with the first and second reservoirs, respectively;
   a first fluid-flow isolation structure located in the second portion;
   a second fluid-flow isolation structure located in the third portion;
   memory for storing a drug-delivery regimen;
   a microprocessor for controlling a delivery of the first and second liquids to a patient through the cannula based on an execution of the stored drug-delivery regimen; and
   a sensor for detecting a measured eye pressure for the patient;
   wherein the first and second fluid-flow isolation structures prevent fluidic communication between the first and second reservoirs and isolate the first and second reservoirs from an external environment.

2. The drug-delivery device of claim 1, wherein each of the first and second therapeutic agents treats at least one of age-related macular degeneration, macular edema associated with diabetic retinopathy, or macular edema associated with retinovascular occlusive diseases.

3. The drug-delivery device of claim 1, wherein each of the first and second therapeutic agents is selected from the group consisting of ranibizumab, pegaptanib, verteporfin, bevacizumab, a steroid, a drug that prevents beta amyloid deposition in the retina, an anti-human complement activation blocker that blocks complement H activation in the eye, and siRNA molecules.

4. The drug-delivery device of claim 1, wherein the first and second therapeutic agents treat two different maladies selected from the group consisting of glaucoma, ocular hypertension, age-related macular degeneration, macular edema associated with diabetic retinopathy, macular edema associated with retinovascular occlusive diseases, low tear production, cytomegalovirus retinitis, bacterial conjunctivitis, itching and allergic conjunctivitis, post-operative eye inflammation, inflammation of the cornea due to herpes simplex virus, postoperative inflammation after cataract extraction, corneal ulcers, and Sjögren's syndrome.

5. The drug-delivery device of claim 1, further comprising first and second pumps for delivering the first and second liquids to the patient, respectively, wherein the microprocessor issues instructions to actuate the first pump separately from the second pump.

6. The drug-delivery device of claim 1, further comprising a sensor for receiving feedback from the patient, the microprocessor being configured to modify the drug-delivery regimen based on the feedback.

7. The drug-delivery device of claim 1, further comprising a sensor for detecting the patient's position and activity, the microprocessor determining at least one of a frequency, time, or dosage of at least one of the first or second liquid delivered to the patient based thereon and responsively controlling delivery of the at least one of the first or second liquid.

8. The drug-delivery device of claim 1, further comprising a transceiver for receiving wireless instructions that reprogram the drug-delivery regimen.

9. The drug-delivery device of claim 1, wherein the sensor monitors physiological effects of at least one of the first or second therapeutic agent present for determining the residual amount of the at least one of the first or second therapeutic agent in the patient's tissue.

10. The drug-delivery device of claim 1, further comprising one or more valves, different from the first and second fluid-flow isolation structures, disposed in the at least one cannula, wherein the one or more valves controls fluid delivery, maintains a constant flow rate independent of variations in pressure driving a fluid flow through the cannula, and prevents backflow.

11. The drug-delivery device of claim 10, further comprising a secondary valve that is independently in fluid communication with the first and second reservoirs for separately controlling fluid delivery therefrom.

12. A drug-delivery device, comprising:
    a first reservoir for containing a first liquid that comprises or consists essentially of a first therapeutic agent;
    a second reservoir for containing a second liquid that comprises or consists essentially of a second therapeutic agent different from the first therapeutic agent;
    a cannula having first, second and third portions, the second and third portions branching off from the first portion to communicate fluidically with the first and second reservoirs, respectively;
    a first fluid-flow isolation structure located in the second portion;
    a second fluid-flow isolation structure located in the third portion;
    an electrolysis chamber including a gas-impermeable flexible membrane configured to expand and contract with increases and decreases in pressure in the electrolysis chamber, the flexible membrane also constituting a portion of at least one of the first or second reservoir;
    at least two electrodes in the electrolysis chamber, the electrodes being responsive to the microprocessor to produce gas in the electrolysis chamber to expand the membrane and thereby force liquid from at least one of the first or second reservoir through the cannula;
    memory for storing a drug-delivery regimen; and
    a microprocessor for controlling a delivery of the first and second liquids to a patient through the cannula based on an execution of the stored drug-delivery regimen
    wherein the first and second fluid-flow isolation structures prevent fluidic communication between the first and second reservoirs and isolate the first and second reservoirs from an external environment.

13. The drug-delivery device of claim 12, further comprising first and second pumps for delivering the first and second liquids to the patient, respectively, wherein the microprocessor issues instructions to actuate the first pump separately from the second pump.

14. The drug-delivery device of claim 12, further comprising a sensor for receiving feedback from the patient, the microprocessor being configured to modify the drug-delivery regimen based on the feedback.

15. The drug-delivery device of claim 12, further comprising a sensor for detecting the patient's position and activity, the microprocessor determining at least one of a frequency, time, or dosage of at least one of the first or second liquid delivered to the patient based thereon and responsively controlling delivery of the at least one of the first or second liquid.

16. The drug-delivery device of claim 12, further comprising a transceiver for receiving wireless instructions that reprogram the drug-delivery regimen.

17. The drug-delivery device of claim 12, further comprising a sensor for detecting a measured eye pressure for the patient.

18. The drug-delivery device of claim 17, wherein the sensor monitors physiological effects of at least one of the first or second therapeutic agent present for determining the residual amount of the at least one of the first or second therapeutic agent in the patient's tissue.

19. The drug-delivery device of claim 12, further comprising one or more valves, different from the first and second fluid-flow isolation structures, disposed in the at least one cannula, wherein the one or more valves controls fluid delivery, maintains a constant flow rate independent of variations in pressure driving a fluid flow through the cannula, and prevents backflow.

20. The drug-delivery device of claim 19, further comprising a secondary valve that is independently in fluid communication with the first and second reservoirs for separately controlling fluid delivery therefrom.

\* \* \* \* \*